US008628789B2

(12) United States Patent
Baughman et al.

(10) Patent No.: US 8,628,789 B2
(45) Date of Patent: Jan. 14, 2014

(54) STRONG REVERSIBLE HYDROGELS

(75) Inventors: Travis Wayne Baughman, Eindhoven (NL); Gaby Maria Leonarda Hoorne-Van Gemert, Landgraaf (NL); Henricus Marie Janssen, Eindhoven (NL); Egbert Willem Meijer, Waalre (NL); Anton Willem Bosman, Eindhoven (NL)

(73) Assignee: SupraPolix, B.V., Eindhoven (NL)

( * ) Notice: Subject to any disclaimer, the term of this patent is extended or adjusted under 35 U.S.C. 154(b) by 1119 days.

(21) Appl. No.: 12/053,404

(22) Filed: Mar. 21, 2008

(65) Prior Publication Data

US 2008/0260795 A1 Oct. 23, 2008

Related U.S. Application Data

(60) Provisional application No. 60/907,177, filed on Mar. 23, 2007.

(51) Int. Cl.
*A61K 9/00* (2006.01)
*C11D 3/37* (2006.01)
*C07D 239/00* (2006.01)

(52) U.S. Cl.
USPC ......... 424/423; 523/105; 514/772.3; 510/475

(58) Field of Classification Search
USPC .............. 424/423, 70.12, 70.11; 528/10, 310, 528/172, 423, 608, 183, 229, 315; 526/72, 526/75; 524/498; 523/105
See application file for complete search history.

(56) References Cited

U.S. PATENT DOCUMENTS

| | | | |
|---|---|---|---|
| 3,375,800 A | 4/1968 | Cole et al. |
| 3,388,087 A | 6/1968 | Dieterich et al. |
| 3,480,592 A | 11/1969 | Dieterich et al. |
| 4,093,759 A | 6/1978 | Otsuki et al. |
| 4,136,092 A | 1/1979 | Jackle et al. |
| 4,140,759 A | 2/1979 | Mausner |
| 4,216,318 A | 8/1980 | Brown et al. |
| 4,229,838 A | 10/1980 | Mano |
| 4,322,327 A | 3/1982 | Yoshimura et al. |
| 4,684,728 A | 8/1987 | Mohring et al. |
| 4,942,035 A | 7/1990 | Churchill et al. |
| 5,410,016 A | 4/1995 | Hubbell et al. |
| 5,500,209 A | 3/1996 | Ross et al. |
| 5,548,035 A | 8/1996 | Kim et al. |
| 5,610,268 A | 3/1997 | Meijer et al. |
| 5,631,337 A | 5/1997 | Sassi et al. |
| 5,723,563 A | 3/1998 | Lawrey et al. |
| 5,736,535 A | 4/1998 | Bernstein et al. |
| 5,874,069 A | 2/1999 | Mendolia et al. |
| 5,883,211 A | 3/1999 | Sassi et al. |
| 5,919,441 A | 7/1999 | Mendolia et al. |
| 6,320,018 B1 | 11/2001 | Sijbesma et al. |
| 6,353,076 B1 | 3/2002 | Barr et al. |
| 6,489,397 B2 | 12/2002 | Kim et al. |
| 6,534,072 B2 | 3/2003 | Mondet et al. |
| 6,683,151 B1 | 1/2004 | Loontjens et al. |
| 6,702,850 B1 | 3/2004 | Byun et al. |
| 6,716,370 B2 | 4/2004 | Kendig |
| 6,743,767 B2 | 6/2004 | Goldoni et al. |
| 6,803,447 B2 | 10/2004 | Janssen et al. |
| 6,803,477 B2 | 10/2004 | Prakash et al. |
| 6,818,018 B1 | 11/2004 | Sawhney et al. |
| 6,899,992 B2 | 5/2005 | Huang et al. |
| 6,911,296 B2 | 6/2005 | Pappas et al. |
| 6,939,938 B2 | 9/2005 | Benard et al. |
| 6,972,304 B2 | 12/2005 | Smith et al. |
| 7,196,073 B2 | 3/2007 | Marciani |
| 7,622,131 B2 | 11/2009 | Bosman et al. |
| 7,736,663 B2 | 6/2010 | Cooper et al. |
| 7,838,621 B2 | 11/2010 | Janssen et al. |
| 7,862,805 B2 | 1/2011 | Mougin et al. |
| 2003/0013631 A1* | 1/2003 | Goldoni et al. ............... 510/475 |
| 2003/0015185 A1 | 1/2003 | Dutart |
| 2003/0079644 A1 | 5/2003 | Smith et al. |
| 2003/0092838 A1 | 5/2003 | Fomperie et al. |
| 2003/0158403 A1 | 8/2003 | Manoharan et al. |
| 2004/0023155 A1 | 2/2004 | Hayakawa et al. |
| 2004/0034190 A1* | 2/2004 | Janssen et al. ............... 528/423 |
| 2004/0087755 A1 | 5/2004 | Eling et al. |
| 2004/0161394 A1 | 8/2004 | Mougin et al. |

(Continued)

FOREIGN PATENT DOCUMENTS

EP 0 259 92 A2 9/1983
EP 0 433 188 A1 6/1991

(Continued)

OTHER PUBLICATIONS

Mooney et al., "Hydrogels for Tissue Engineering" Chem. Rev. 101, p. 1869, 2001.
Sijbesma et al., "Reversible Polymers Formed from Self-Complementary Monomers Using Quadruple Hydrogen Bonding" Science, 278, 1601.
Lange et al., Hydrogen-Bonded Supramolecular Polymer Networks: J. Polym. Sci. A, 1999, 3657.
Kautz et al., Cooperative End-to-End and Lateral Hydrogen-Bonding Motifs in Supramolecular Thermoplastic Elastomers: (Macromolecules , 2006, 39, 4265).
Handbook of Chemistry & Physics, $59^{th}$ Ed., p. E-61, 1978-1979.
Yamauchi K, et al., "Thermoreversible Poly(alkyl acrylates) Consisting of Self-Complementary Multiple Hydrogen Bonding" Macromolecules 2003, 36, No. 4, 1083-1088.
Ky Hirschberg J.H.K., et al., "Ureidotriazine-Based Supramolecular Copoloymers" Marcomolecules, 2003, 36, No. 5, 1429-1432.
Brunsveld, L et al., "Supramolecular Polymers", Chemical Reviews, vol. 101, 2001, pp. 4071-4097, XP002267453.
Chemical Abstract, vol. 85, Abst. No. 15348y, Jul. 1976, 1 Page.
Chemical Abstracts, Vo. 97, No. 10, Sep. 1982, Veselovskii et al., "Adhesive Composition," Inst. of the Chemistry of High Molecular Weight Compounds, Mar. 5, 1979, 1 Page.
Chemical Abstracts, vol. 80, No. 20, May 20, 1974, English abstract of JP 04 829398, filed Aug. 28, 1968, 1 Page.
Derwent 91-179975125, 1 Page.

(Continued)

Primary Examiner — James J Seidleck
Assistant Examiner — S. Camilla Pourbohloul
(74) Attorney, Agent, or Firm — Gilberto M. Villacorta; Sunit Talapatra; Foley & Lardner LLP

(57) ABSTRACT

The present invention relates to improved hydrogel materials using water gellants that are comprised of polymer backbones P to which hydrogen bonding 4H-units are covalently attached via a hydrophobic linker L. Optionally, the hydrogel contains additional ingredients or additives. These new reversible hydrogels can easily be fine-tuned in their mechanical performance and function and are especially suitable for biomedical applications.

22 Claims, No Drawings

(56) References Cited

U.S. PATENT DOCUMENTS

| | | |
|---|---|---|
| 2007/0149751 A1 | 6/2007 | Lindsay et al. |
| 2007/0264208 A1 | 11/2007 | Mougin et al. |
| 2009/0111930 A1 | 4/2009 | Van Gemert et al. |
| 2010/0076147 A1 | 3/2010 | Hoorne-Van Gemert et al. |
| 2011/0034641 A1 | 2/2011 | Janssen et al. |
| 2012/0116014 A1 | 5/2012 | Janssen et al. |

FOREIGN PATENT DOCUMENTS

| | | |
|---|---|---|
| EP | 0 744 428 A2 | 11/1996 |
| EP | 0 683 769 B1 | 7/1998 |
| EP | 0 877 055 A | 11/1998 |
| EP | 1 213 309 A | 6/2002 |
| EP | 1 310 533 A2 | 5/2003 |
| EP | 1 687 378 A1 | 8/2006 |
| EP | 1 392 222 | 9/2007 |
| EP | 2 450 394 A1 | 5/2012 |
| FR | 2825628 B1 | 12/2002 |
| JP | 48-029398 B | 9/1973 |
| JP | 51-022823 A | 2/1976 |
| JP | 52-074692 A | 6/1977 |
| JP | 2004-250623 A | 9/2004 |
| SU | 910718 A1 | 3/1982 |
| WO | WO-98/14504 A1 | 4/1998 |
| WO | WO-98/14505 A1 | 4/1998 |
| WO | WO-98/23307 | 6/1998 |
| WO | WO 99/07343 | 2/1999 |
| WO | WO 01/44307 | 6/2001 |
| WO | WO-02/34312 A1 | 5/2002 |
| WO | WO-02/46260 A1 | 6/2002 |
| WO | WO 02/098377 | 12/2002 |
| WO | WO-03/032929 A2 | 4/2003 |
| WO | WO-03/059964 A2 | 7/2003 |
| WO | WO-03/099875 A2 | 12/2003 |
| WO | WO-2004/016598 A1 | 2/2004 |
| WO | WO 2004/052963 A | 6/2004 |
| WO | WO 2005/042641 A1 | 5/2005 |
| WO | WO-2006/006855 A1 | 1/2006 |
| WO | WO 2006/118460 A1 | 11/2006 |
| WO | WO 2006/118461 A2 | 11/2006 |
| WO | WO-2007/058539 A2 | 5/2007 |
| WO | WO-2007/072000 A1 | 6/2007 |
| WO | WO-2008/063057 A3 | 5/2008 |

OTHER PUBLICATIONS

Derwent Abstract Acc. No. 1977-55084Y, Week 197731, English abstract for JP 52-74692, Jun. 22, 1977, 3 Pages.

Dieterich et al, "Polyurethane Ionomers, a New Class of Block Polymers," Angew. Chem. Int'l. Edit., vol. 9, No. 1, 1970, p. 40-50 (English version of German article in Angew. Chem., vol. 2, 1970, p. 53-63).

El-Ghayoury et al., "Supramolecular Hydrogen-Bonded Oligo(p-phenylene vinylene) Polymers," Angew. Chem. Intl. Ed., vol. 40, No. 19, 2001, pp. 3660-3663. XP002260390.

Flory, P.J., "Random Reorganization of Molecular Weight Distribution in Linear Condensation Polymers," J. Am. Chem. Soc., 1942, vol. 64, pp. 2205-2212.

Folmer et al., "Supramolecular Polymer Materials: Chain Extension of Telechelic Polymers Using a Reactive Hydrogen-Bonding Synthon," Adv. Mater., vol. 12, No. 12, 2000, p. 874-878.

Guan et al., "Modular Domain Structure: A Biomimetic Strategy for Advanced Polymeric Materials," J. Am. Chem. Soc., vol. 126, 2004, pp. 2058-2065.

Guan et al., "Synthesis and Single-Molecule Studies of Modular Polymers Using Precise Hydrogen Bonding Interactions," Polymer Preprints, vol. 44(2), 2003, pp. 485-486.

Hirschberg et al., "Supramolecular Polymers from Linear Telechelic Siloxanes with Quadruple-Hydrogen-Bonded Units," Macromolecules, vol. 32, No. 8, 1999, pp. 2696-2705.

Hofmeier et al., "New Supramolecular Polymers Containing Both Terpyridine Metal Complexes and Quadruple Hydrogen Bonding Units," Chem. Commun., 2004, pp. 318-319.

Kato T., "Supramolecular Liquid Crystal Polymers, Formation of Molecular Self-Organized Structures and Their Functionalization," Kobunshi Ronbunshu, vol. 54(12), 1997, pp. 855-862. (Abstract on last page).

Korshak et al., "Experimental Methods of Bulk Polymerization," Comprehensive Polymer Science: The Synthesis, Characterization, Reactions & Application of Polymers, vol. 5, 1989, Pergamon Press, pp. 131-142.

Lange et al., "Supramolecular Polymer Interactions Based on the Alternating Copolymer of Styrene and Maleimide," Macromolecules, vol. 28, 1995, pp. 782-783.

Rieth et al., "Polymerization of Ureidopyrimidinone-Functionalized Olefins by Using Late-Transition Metal Ziegler-Natta Catalysts: Synthesis of Thermoplastic Elastomeric Polyolefins," Angew. Chem. Intl. Ed., vol. 40, No. 11, 2001, pp. 2153-2156.

Roland et al., "Synthesis of Titin-Mimicking Polymers Having Modular Structures by Using Noncovalent Interactions", Polymer Preprints, vol. 44(1), 2003, pp. 726-727.

Saunders et al. (editors), "Polyurethanes—Chemistry and Technology High Polymers: Part 1. Chemistry," High Polymers, vol. XVI-Part 1, 1962, Interscience Publishers a Division of Wiley & Sons, pp. 68-73.

Urbanski et al. "Potential Antimalarial Compounds.sup.1. $IX^2$. Pyrimidine Derivatives of Urea and Guanidine", Journal of Medicinal Chemistry, vol. 10, 1967, p. 521-525.

Yamauchi et al., Abstract of "Synthesis and Characterization of Novel Multiple-Hydrogen Bonded Macromolecules Via A Michael Reaction," Dept. of Chemistry, Virginia Polytechnic Institute and State University.

Yamauchi, et al., "Thermoreversible Polyesters Consisting of Multiple Hydrogen Bonding (MHB)," Macromolecules, vol. 37, No. 10, 2004, pp. 3519-3522.

Cate et al., "Hydrogen-Bonded Supramolecular Polymers with Tunable Material Properties," Polymer Preprints, 44(1):618-619 (2003).

Even et al., "Synthesis and Characterization of Amphiphilic Triblock Polymers by Copper Mediated Living Radical Polymerization," European Polymer Journal, 39:633-639 (2003).

Hirschberg et al., "Helical Supramolecular Aggregates Based on Ureidopyrimidinone Quadruple Hydrogen Bonding," Chemistry—A European Journal, 9:4222-4231 (2003).

Kiriy et al., "Atomic Force Microscopy Visualization of Single Star Copolymer Molecules," Polymeric Materials: Science & Engineering, 88:233-234 (2003).

Matsuda et al., "Terminally Alkylated Heparin. 1. Antithrombogenic Surface Modifier," Biomacromolecules, 2:1169-1177 (2001).

Maynard et al., "Inhibition of Cell Adhesion to Fibronectin by Oligopeptide-Substituted Polynorbornenes," Journal of American Chemical Society, 123:1275-1279 (2001).

Menger et al., "Self-Adhesion Among Phospholipd Vesicles," Journal of the American Chemical Society, 128:1414-1415 (2006).

Rowley et al., "Alginate Hydrogels as Synthetic Extracellular Matrix Materials," Biomaterials, 20:45-53 (1999).

Uhrich et al., "Polymeric Systems for Controlled Drug Release," Chemical Reviews, 99:3181-3198 (1999).

Vulic et al., "Heparin-Containing Block Copolymers," Journal of Materials Science: Materials Medicine, 4:353-365 (1993).

\* cited by examiner

STRONG REVERSIBLE HYDROGELS

CROSS-REFERENCE TO RELATED PATENT APPLICATIONS

This application claims priority from U.S. Provisional Application No. 60/907,177, filed Mar. 23, 2007, which is incorporated herein by reference in its entirety.

FIELD OF THE INVENTION

This invention relates to new hydrogel materials that comprise water gellants comprising hydrophilic polymers to which several hydrogen bonding units are covalently attached via an apolar motif so that they are cross-linked in a reversible supramolecular way by hydrogen bonds. As the water gellants are physically or non-covalently cross linked, the hydrogel materials are more easily processed. In addition, fine-tuning of the material properties of such hydrogel materials (e.g. mechanical strength or elasticity, degradation behavior) can be controlled more easily.

BACKGROUND OF THE INVENTION

Structurally, hydrogels are three-dimensional networks of polymer chains with a high content of absorbed water molecules. Hydrogels find applications in for example medical applications including bone transplants and tissue adhesives, drug delivery systems, pharmaceuticals and in water management.

Hydrogels can occur in the cross-linked form or in the uncross-linked form. Cross-linking usually provides higher viscosities due to an apparent or real increase of the molecular weight and often results into the formation of gels.

Cross-linking can be achieved chemically by the formation of covalent bonds or physically by the formation of e.g. hydrogen bonds or ionic interactions. Obviously, cross-linking can also be achieved both chemically and physically.

Chemical cross-linking of hydrophilic polymers is a general and often applied route to obtain hydrogels. In order to be able to administer or process these gels, prepolymers are dissolved in water and are then polymerized resulting in (in situ) hydrogel formation. Hydrogellation procedures are often based on the use of acrylic or methacrylic macromonomers that are not preferred in (biomedical) applications, because of their inherent toxicity and because they usually require an auxiliary, potentially hazardous, initiator for polymerization. Moreover, chemically cross-linked hydrogels lack reversibility and are limited in their degradation behavior, as poly(acrylate)s and poly(methacrylate)s are not biodegradable. For example, U.S. Pat. No. 5,410,016 discloses hydrogels based on copolymers of poly(ethylene glycol) with poly(DL-lactide) containing pendant acrylate functions that are cross-linked in situ. WO 01/44307 discloses hydrogels based on polyvinyl alcohol modified with pendant acrylate and methacrylate groups that are chemically cross-linked in situ. Hence, according to these prior art references, an irreversible cross-linked hydrogel is obtained by starting from water processable prepolymers that contain reactive groups.

Hydrogels based on natural polymers, especially collagen, are biocompatible and mostly thermally reversible (Mooney et al. Chem. Rev. 101, page 1869, 2001). However, the mechanical properties of these gels are limited and hardly, if at all, tunable. Especially the mechanical strength in these materials is too low, and often an additional chemical modification is required to make them stronger. However, this results in a reduced biocompatibility and a reduced biodegradation.

U.S. Pat. No. 4,942,035 and U.S. Pat. No. 5,548,035 disclose hydrogels based on block-copolymers in which hydrophilic blocks are alternated by hydrophobic blocks. For example, U.S. Pat. No. 4,942,035 discloses a triblock copolymer consisting of a polyethylene glycol middle block surrounded by two poly(D,L-lactide-co-glycolide) polyester blocks (weight ratio of polyester to PEG at least 1) was prepared and showed gelling behaviour in water. The hydrogels are formed because of phase separation of the hard hydrophobic polyester block, and consequently the relative amount of the hydrophobic polymer needs to be high to counterbalance the hydrophilicity of the polyethylene glycol block to guarantee the gelling behaviour. Therefore, the range of mechanical properties of these gels is limited—for examples with respect to the elasticity—as these properties are mainly governed by the hard block.

WO 99/07343 discloses thermally reversible hydrogels intended for uses in drug delivery applications that are based on a hydrophilic polyethylene glycol block and hydrophobic PLLA (poly-L-lactic acid) blocks. The gelling is governed by the presence of the crystalline hard blocks formed by the PLLA. The presence of the crystalline PLLA-blocks limits the mechanical properties and the biodegradation of these materials to a great extent.

U.S. Pat. No. 6,818,018 discloses hydrogels that can be formed in a mammal in situ by providing a system comprising a first polymer that is capable to form physical cross-links and a second polymer that is capable to form chemical cross-links. The first polymer may be selected from a wide group of materials including ionomers whereas the second polymer may be selected from virtually any material that has chemical groups capable of forming covalent bonds.

U.S. Pat. No. 5,883,211 discloses a thermo-reversible hydrogel comprising a physically cross-linked copolymer based on poly(acrylamide) containing up to six different monomers with hydrogen bonding N-substituent groups. The relative content of these monomers with hydrogen bonding N-substituent groups in the copolymer needs to be higher than 50% to display thermo-reversible gelling behaviour.

In general, "supramolecular chemistry" is understood to be the chemistry of physical or non-covalent, oriented, multiple (at least two), co-operative interactions. For instance, a "supramolecular polymer" is an organic compound that has polymeric properties—for example with respect to its rheological behaviour—due to specific and strong secondary interactions between the different molecules. These physical or non-covalent supramolecular interactions contribute substantially to the properties of the resulting material.

Supramolecular polymers comprising (macro)molecules that bear hydrogen bonding units can have polymer properties in bulk and in solution, because of the hydrogen bridges between the molecules. Sijbesma et al. (see U.S. Pat. No. 6,320,018 and Science, 278, 1601) have shown that in cases where a self-complementary quadruple hydrogen bonding unit (4H-unit) is used, the physical interactions between the molecules become so strong that materials with much improved properties can be prepared.

A poly(ethylene-propylene) oxide co-polymer (PEO-PPO-polymer) having three alcohol end groups was modified with 4H-units (cf. Lange et al. J. Polym. Sci. A, 1999, 3657 and WO 02/098377). The modified polymer was soluble in organic solvents such as chloroform and THF and it appeared that the viscosity of the polymer was significantly effected by the polarity of the solvent. For example, addition of water to a solution of the polymer resulted in a significant decrease of the viscosity due to breaking of the hydrogen bonds between polymer molecules and formation of hydrogen bonds between polymer molecules and water molecules. However, the viscosity was still much higher than that of a reference-solution of a low molecular weight compound bearing one 4H-unit. Due to the relatively high PPO-content (63%) of the PEO-PPO copolymer, this material will hardly, if at all, dissolve in water and the polymers have not been tested in water.

EP A 1392222 discloses inter alia a telechelic poly(ethylene-propylene)oxide co-polymer (PEO-PPO-polymer) having three alcohol end groups that is modified with 4H-units resulting in a non-waterprocessable polymer. Nevertheless, in example C of this patent a hairstyling gel is disclosed with only 0.2 wt % of the PEO-PPO-polymer containing 4H-units, in an aqueous composition that further contains 1.0 wt % of a gelling agent based on cross-linked high molecular weight polyacrylate and 17 wt % ethanol as co-solvent. Apparently, the high ethanol content is needed to make the PEO-PPO polymer processable, and the polyacrylate is required to get a gel composition.

US 2003/0079644 discloses ink additives comprising 2-4 4H-units that are prepared from e.g. PEO-PPO polymers commercially available under the trade name VORANOL® from Dow Chemical Co., Midland, Mich., US, and 2(6-isocyanato-hexylaminocarbonylamino)-6-methyl-4(1H)-pyrimidone. According to the Examples XIII-XVI of US 2003/0079644, the ink compositions may comprise up to 5 wt. % of the polymer and water in the range of about 18 to about 35 wt. % and these compositions would have a viscosity at about 25° C. of no more than about 10 cP (cf. paragraphs [0174] and [0179] of US 2003/0079644). This implies that these polymers are not water gellants.

Kautz et al. (Macromolecules, 2006, 39, 4265) show by AFM measurements that in telechelic poly(ethylene-butylene)polymers modified with 4H-units, the phase separation of the 4H-units is more pronounced when polymer backbone and 4H-unit are connected via a urea group when compared to a urethane connecting group. The mechanical properties of the urea-based polymer are not better, but worse, as evidenced by tensile testing results. Also, the presented materials cannot be used for hydrogel formulations due to their lack of hydrophilicity.

WO 2006/118460 discloses hydrogel materials comprising water gellants that are comprised by hydrophilic polymers to which at least two 4H-units are covalently attached via urethane-alkyl moieties. However, it appeared that these hydrogel materials are insufficient in strength for several applications. In addition, in some examples a toxic Sn-catalyst is employed and the presence of residues of such catalysts are undesired, in particular when the hydrogel materials are intended for biomedical applications.

WO 2006/118461 discloses modular supramolecular bioresorbable or biomedical material comprising (i) a polymer comprising at least two 4H-units and (ii) a biologically active compound. The supramolecular bioresorbable or biomedical material is especially suitable for biomedical applications such as controlled release of drugs, materials for tissue-engineering, materials for the manufacture of a prosthesis or an implant, medical imaging technologies.

Because of the reviewed shortcomings of state-of-the-art hydrogels, there is a need for synthetic polymers that are able to gel water reversibly, implying that the hydrogels can be switched between a gelled state and a liquid state. This would facilitate easy processing and administration of these hydrogels. In addition, it is desired that reversible hydrogels can be made that are elastic and that have high strengths. It would also be advantageous to be able to make biodegradable reversible hydrogels. Finally, in view of biomedical applications for hydrogels, it would be very beneficial to be able to make water gellants and their hydrogels in a quality-controlled fashion.

SUMMARY OF THE INVENTION

It is an object of the present invention to provide new hydrogels comprising a polymeric water gellant, water and optionally another solvent and a process to prepare such new hydrogels, preferably without the use of a toxic metal-based catalyst. With this invention, easy preparation of hydrogels is enabled without the need for chemical cross-linking procedures. The hydrogels according to the invention combine easy processing and administration with good and tunable mechanical properties, while it is optional to make the hydrogels biodegradable.

The present invention therefore relates to a hydrogel comprising:

(a) 0.3-50.0 wt. %, based on the total weight of the hydrogel, of a water gellant comprising a polymer backbone P having the structure according to formula (A) or formula (B):

$$P\text{-}[L\text{-}(4H)_n] \qquad (A)$$

or

$$[P\text{-}L\text{-}(4H)\text{-}L\text{-}]_p \qquad (B)$$

wherein:

n is in the range of 1.8 to 10;

p is in the range of 2 to 25;

L is a hydrophobic linker selected from the group consisting of cyclic, linear or branched $C_2$-$C_{24}$ alkylene groups, $C_6$-$C_{24}$ arylene groups, $C_7$-$C_{24}$ alkarylene groups and $C_7$-$C_{24}$ arylalkylene groups, wherein the alkylene groups, arylene groups, alkarylene groups and arylalkylene groups optionally, but not preferably, comprise 1-5 heteroatoms selected from the group consisting of O, N and S, and wherein said hydrophobic linker L is covalently connected to the 4H-unit via an urea or via an amide moiety; and wherein 4H represents the 4H-unit that has the general formula (1) or (2):

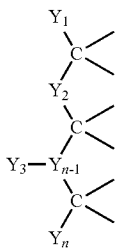

(2)

wherein the C—$X_i$ and the C—$Y_i$ linkages each represent a single or double bond, n is 4 or more, and $X_i$ represent donors or acceptors that form hydrogen bridges with the H-bridge forming monomeric unit containing a corresponding general form (2) linked to them with $X_i$ representing a donor and $Y_i$ an acceptor and vice versa; and (b) 50.0 to 99.7 wt. % water.

In another embodiment of this invention, the water gellant is constructed from a polymer backbone P to which at least 1.8 urea or amide hydrogen bonding units are connected via a hydrophobic linker L. The urea or amide functions are more simple hydrogen bonding units than the 4H-unit.

DETAILED DESCRIPTION OF THE INVENTION

It was surprisingly found that hydrogels based on water gellants comprising hydrophilic polymers comprising 4H-units could be improved in their mechanical performance when the 4H-unit was linked to the polymer backbone with a hydrophobic linker L, where this hydrophobic linker L was covalently connected to the 4H-unit with an urea or an amide moiety. The novel hydrophilic polymers are prepared by a versatile synthetic method. Moreover, this method does not require toxic (metal) catalysts, which makes the water gellants more suitable for biomedical applications.

The reversibility of the supramolecular hydrogen bonding interaction allows for reversible switching between a gelled state and a liquid state by changing the temperature, the concentration of polymeric gellant, or the polarity or ionic strength of the solvent, and therefore makes it possible to easily process or administer the hydrogel for the desired application. Moreover, the reversible supramolecular interaction can also favour the biodegradation of the hydrogel material.

In this document, the structure of the water gellant according to this invention and its preparation are disclosed, as well as the components of the gellant: (i) the hydrogen bonding 4H-unit, (ii) the polymer backbone P and (iii) the hydrophobic linker L. Finally, the hydrogels that can be prepared from the newly prepared water gellants are disclosed.

GENERAL DEFINITIONS

An urea moiety as indicated in this document is to be understood as a moiety according to the formula:

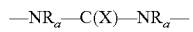

wherein X is O or S, preferably O, $R_a$ is, independently, a hydrogen atom or a linear, branched or cyclic $C_1$-$C_{12}$ alkyl group, preferably hydrogen, or a linear, branched or cyclic $C_1$-$C_6$ alkyl group, most preferably a hydrogen.

An amide moiety as indicated in this document is to be understood as a moiety according to the formula:

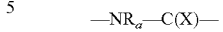

wherein X and $R_a$ are as described above.

An urethane moiety as indicated in this document is to be understood as a moiety according to the formula:

wherein X and $R_a$ are as described above (X can independently be O or S).

An ester moiety as indicated in this document is to be understood as a moiety according to the formula:

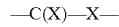

wherein X is as described above (X can independently be O or S).

A carbonate moiety as indicated in this document is to be understood as a moiety according to the formula:

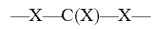

wherein X is as described above (X can independently be O or S).

An amine moiety as indicated in this document is to be understood as a moiety according to the formula:

wherein $R_a$ is as described above.

An ether moiety as indicated in this document is to be understood as a moiety according to the formula:

wherein X is as described above.

An isocyanate group is to be understood as a —NCX group, wherein X is as described above.

Acrylate and methacrylate groups are to be understood as $R_b$—C(=$CH_2$)—C(X)—X— groups, wherein X is as described above (X can independently be O or S), and wherein $R_b$ is hydrogen or methyl. It is, however, preferred that in acrylate and methacrylate groups X is O.

Acrylamide and methacrylamide groups are $R_b$—C(=$CH_2$)—C(X)—N($R_3$)— groups, wherein X and $R_1$ are as described above, and wherein $R_b$ is hydrogen or methyl. It is, however, preferred that in acrylamide and methacrylamide groups X is O.

The verb "to comprise" as is used in this description and in the claims and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

The Structure of the Water Gellant and its Preparation

The water gellant of this invention has the general structure

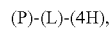

where P represents the polymer backbone to which the 4H-unit is covalently connected via the hydrophobic linker L.

The water gellant has a molecular weight of 1200 to 1,000,000, preferably 2000 to 100,000, more preferably 3000 to 80,000, more preferably 5000 to 50,000 and most preferably 7,500 to 21,000 Dalton.

The 4H-units can be attached to the polymer backbone P via the hydrophobic linker L in any way, e.g. by grafting onto the polymer backbone, by attachment to multiple—i.e. two or more—end groups of the polymer backbone, or the 4H-units can be an integral part of the backbone of the polymer that constitutes the water gellant. As will be understood by the person skilled in the art, the 4H-units may also be attached by a combination of these bonding modes.

It is preferred that the polymer backbone P and the hydrophobic linker L are connected via a (thio)urea, (thio)urethane, amide, ester, carbonate, secondary amine, tertiary amine or ether moiety, more preferably a urethane, urea or ether group, most preferably a urethane group.

The hydrophobic linker L is preferably connected to the 4H-unit via a (thio)urea, (thio)urethane, amide, ester, carbonate, secondary amine, tertiary amine or ether moiety. It is, however, more preferred that the hydrophobic linker L and the 4H-unit are connected via a (thio)urea or an amide moiety, even more preferably via a urea or amide moiety, most preferably via a urea moiety.

More preferably, the water gellant of this invention has the structure P-[L-(4H)]$_n$ or the structure [P-L-(4H)-L-]$_p$. Most preferably, the water gellant has the general structure [P-L-(4H)-L-]$_p$.

In the structure P-[L-(4H)]$_n$, structure (A), the polymer backbone P is multifunctional and has n 4H-units connected to it via the hydrophobic linker L. The functionality n is at least 1.8, and is preferably 1.8 to 10, more preferably 1.8 to 5, even more preferably 1.8 to 3, most preferably 1.8 to 2, in which case the water gellant is preferably telechelic and has the general structure:

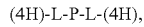

(4H)-L-P-L-(4H), in which the backbone P is at each of the two sides connected to a 4H-unit via the hydrophobic linker L. Due to a somewhat lesser definition of the telechelic material, the functionality n may be as low as 1.8, but is preferably higher than 1.9, most preferably higher than 1.95.

In the structure [P-L-(4H)-L-]$_p$, structure (B), the polymer backbone P is covalently chain extended with the 4H-unit via the hydrophobic linker L. Here, the number of repeating units p is at least 2, more preferably at least 3, most preferably at least 4. It is preferred that p is not higher than 25.

The hydrophobic linker L can be introduced into the water gellant by two methods: (a) the hydrophobic linker L is covalently attached to the polymer backbone P and thereafter the resulting functional prepolymer is connected to a 4H-unit building block to produce the water gellant or, (b) the hydrophobic linker L is attached to the 4H-unit and the resulting functional building block is covalently attached to the polymer backbone P to produce the water gellant.

Method (a) is preferred, and in this method the functional prepolymer is preferably denoted as P-[L]$_n$, where n represents the number of hydrophobic groups that are attached to the polymer backbone P. Preferably, n is at least 1.8, more preferably n is 1.8 to 10, more preferably 1.8 to 5, even more preferably 1.8 to 3, most preferably 1.8 to 2, in which case the prepolymer is preferably telechelic and can be denoted as L-P-L, where the backbone P is at each of the two sides connected to a functional hydrophobic group L. Due to a somewhat lesser definition of the telechelic material, the functionality n may be as low as 1.8, but is preferably higher than 1.9, most preferably higher than 1.95. The functional groups attached to the hydrophobic linkers L are preferably secondary or primary amine groups, most preferably primary amine groups.

Accordingly, the present invention relates to a method for the preparation of a water gellant having the formula (A) or the formula (B):

P-[L-(4H)]$_n$     (A)

or

[P-L-(4H)-L-]$_p$     (B)

wherein in a first step a polymer backbone P is converted into a prepolymer according to the formula P-[L]$_n$, and wherein in a second step the 4H-unit is introduced at the termini of the hydrophobic linker moiety L, wherein P, L and the 4H-unit are connected to each other by moieties selected from the group consisting of (thio)urea, (thio)urethane, amide, ester, carbonate, secondary amine, tertiary amine and ether moieties. As will be apparent to the skilled person, the polymer backbone P, the hydrophobic linker L and the 4H-unit are furnished with functional groups that are capable in providing the connecting moieties described above.

In method (b), the hydrophobic linker L is attached to the 4H-unit to produce the building block 4H-[L]$_q$, wherein q represents the number of hydrophobic linker groups L attached to the 4H-unit. Preferably, q is 1 or 2, most preferably q is 1. The functional group attached to the hydrophobic linker L in building block 4H-[L]$_q$ is preferably an isocyanate, amine, acrylate, methacrylate, acrylamide, methacrylamide or hydroxy group, more preferably an amine or isocyanate group, most preferably an amine.

Accordingly, the present invention also relates to a method for the preparation of a water gellant having the formula (A) or the formula (B) that are shown above, wherein in a first step a hydrophobic linker L is functionalised at a first terminus thereof with a 4H-unit to provide a building block having the structure 4H-[L]$_q$, wherein q represents the number of hydrophobic linker groups L attached to the 4H-unit and wherein q is 1 or 2, wherein the hydrophobic linker has a functional group at the other terminus, and wherein in a second step the building block having the structure 4H-[L]$_q$ is connected to the polymer backbone P. The backbone P, the linker L and the 4H-unit are connected to each other by moieties selected from the group consisting of (thio)urea, (thio)urethane, amide, ester, carbonate, secondary amine, tertiary amine and ether moieties. As will be apparent to the skilled person, the polymer backbone P, the hydrophobic linker L and the 4H-unit are furnished with functional groups that are capable in providing the connecting moieties described above.

In a less preferred embodiment of this invention, the amine functional prepolymer P-[L]$_n$ as prepared in above mentioned method (a) is reacted with a mono- or difunctional compound to produce water gellants in which the polymer backbone P is linked to a simple hydrogen bonding unit via the hydrophobic linker L. The simple hydrogen bonding unit can be any hydrogen bonding unit known in the art, but is preferably a (thio)urea, an amide, or a (thio)urethane. More preferably, it is an urea or an amide, most preferably an urea. Accordingly, the mono- or difunctional compounds are preferably (di)isocyanates, (di)thioisocyanates, (di)amines which are optionally activated, (di)acid chlorides, (di)esters which are optionally activated, (di)ols which are optionally activated, (di)acryl amides, (di)methacryl amides or (di)thiols which are optionally activated, preferably (di)isocyanates, (di) activated amines or (di) activated esters, most preferably (di)isocyanates. Non-limiting examples are hexylisocyanate, dodecylisocyanate, 1,6-hexyldiisocyanate, 1,10-decyldiisocyanate, isophorone diisocyanate, adipoyl chloride, glutaryl chloride, succinyl chloride, undecenoyl chloride, and the like.

Also in this less preferred embodiment, for P-[L]$_n$, n is preferably 1.8 to 10, more preferably 1.8 to 5, even more preferably 1.8 to 3, most preferably 1.8 to 2, in which case the amine functional polymer is preferably telechelic, and n is preferably 1.9 to 2, most preferably 1.95 to 2. When n=1.8 to 2, the compounds with which P-[L]$_n$ are reacted can be monofunctional (i.e. a capping reaction) or difunctional (i.e. a chain extension reaction), preferably difunctional. When n is greater than 2, the compound is monofunctional (i.e. a capping reaction).

The water gellant according to this embodiment of the invention has a molecular weight of 1200 to 1,000,000, preferably 2000 to 100,000, more preferably 3000 to 80,000, more preferably 5000 to 50,000 and most preferably 7,500 to 21,000 Dalton.

The 4H-Unit

The 4H-unit of this invention has the general formula (1) or (2):

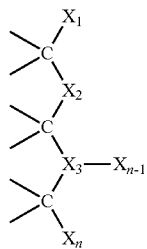

(1)

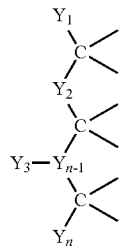

(2)

wherein the C—X$_i$ and the C—Y$_i$ linkages each represent a single or double bond, n is 4 or more, and X$_i$ represent donors or acceptors that form hydrogen bridges with the H-bridge forming monomeric unit containing a corresponding general form (2) linked to them with X$_i$ representing a donor and Y$_i$ an acceptor and vice versa. It is preferred that the 4H-unit is an essentially planar or flat structure.

It is also preferred that in formulas (1) and (2) n equals 4 so that the 4H-unit comprises four donors or acceptors X$_1$ ... X$_4$ and Y$_1$ ... Y$_4$. The 4H-unit may be self-complementary (i.e. the two hydrogen bonded units X$_1$ ... X$_4$ and Y$_1$ ... Y$_4$ have an equal array of donors and acceptors), or non self-complementary (i.e. the two hydrogen bonded units X$_1$ ... X$_4$ and Y$_1$ ... Y$_4$ have two different arrays of donors and acceptors). Preferably, the 4H-unit comprises two successive donors, followed by two successive acceptors, i.e. that it is preferred that X$_1$ and X$_2$ are donors and X$_3$ and X$_4$ are acceptors. Preferably, the donors and acceptors are O, S, and N atoms. The 4H-unit is in detail disclosed in U.S. Pat. No. 6,320,018 which is incorporated by reference herein.

According to a preferred embodiment of the present invention the 4H-unit has the general formula (3) or formula (4) and tautomers thereof:

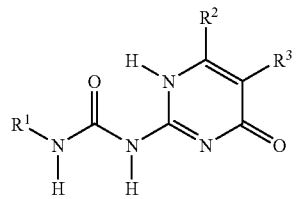

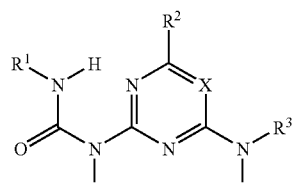

wherein X is a nitrogen atom or a carbon atom bearing a substituent R$^{15}$, preferably X is a nitrogen, and wherein R$^1$, R$^2$, R$^{15}$ and R$^3$ are selected from the group consisting of:
(a) hydrogen;
(b) C$_1$-C$_{20}$ alkyl;
(c) C$_6$-C$_{12}$ aryl;
(d) C$_7$-C$_{12}$ alkaryl;
(e) C$_7$-C$_{12}$ alkylaryl;
(f) polyester groups having the formula (5)

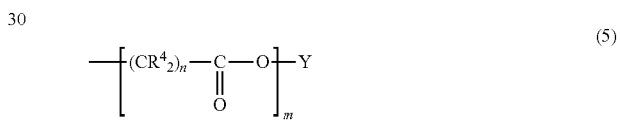

wherein R$^4$ and Y are independently selected from the group consisting of hydrogen and C$_1$-C$_6$ linear or branched alkyl, n is 1-6 and m is 10 to 100;
(g) C$_1$-C$_{10}$ alkyl groups substituted with 1-4 ureido groups according to the formula (6)

R$^5$—NH—C(O)—NH— (6)

wherein R$^5$ is selected from the group consisting of hydrogen and C$_1$-C$_6$ linear or branched alkyl;
(h) polyether groups having the formula (7)

wherein Y, R$^6$ and R$^7$ are independently selected from the group consisting of hydrogen and C$_1$-C$_6$ linear or branched alkyl and o is 10-100, and
wherein the 4H-unit is bonded to the polymer backbone P via R$^1$, R$^2$ and/or R$^3$ (so that R$^1$, R$^2$ or R$^3$ represent a direct bond) with the other R groups representing, independently a side chain according to (a)-(h).

As will be apparent to the person skilled in the art, the groups (b)-(h) defined above may be linear, branched or cyclic where appropriate.

In a first preferred embodiment, the 4H-unit is bonded to the polymer backbone P via R$^1$ (so that R$^1$ constitutes a direct bond), while R$^2$ and R$^3$ are independently any one of the groups (a)-(h) defined above, preferably group (a) or group (b), more preferably for group (b) 2-ethylpentyl, n-decyl, n-tridecyl, n-pentyl or methyl and most preferably methyl.

Most preferably, the 4H-unit is bonded to the polymer backbone via $R^1$, whereas $R^2$ is any one of the groups (a)-(h) defined above, more preferably group (b), even more preferably 2-ethylpentyl, n-decyl, n-tridecyl, n-pentyl or methyl and most preferably methyl, and $R^3$ is hydrogen.

In a second preferred embodiment, the 4H-unit is bonded to a polymer backbone P via $R^1$ and $R^2$ (so that $R^1$ and $R^2$ constitute direct bonds), while $R^3$ is any one of the groups (a)-(h) defined above, preferably group (a) or (b), more preferably group (a) or the 4H-unit is bonded to a polymer backbone P via $R^1$ and $R^3$ (so that $R^1$ and $R^3$ constitute a direct bond), while $R^2$ is any one of the groups (a)-(h) defined above, preferably group (b), more preferably isopropyl or methyl and most preferably methyl. Most preferably for this embodiment, the 4H-unit is bonded to a polymer backbone P via $R^1$ and $R^3$, while $R^2$ is any one of the groups (a)-(h) defined above, preferably group (b), more preferably isopropyl or methyl and most preferably methyl.

The 4H-unit building blocks that are used to prepare the water gellants of this invention are furnished with functional groups that are part of the residues $R^1$, $R^2$ or $R^3$. Also when the $R^1$, $R^2$ or $R^3$ residues are furnished with functional groups for coupling to the polymer backbone P, these residues do specifically not contain the linker L. The functional groups can be any functionalities known in the art, but are preferably (thio) isocyanates, (activated) amines, alcohols, thiols, (activated) esters, acrylates, methacrylates, acryl amides, methacryl amides or other vinyl groups, more preferably isocyanates, (activated) amines, acrylates, methacrylates or alcohols, even more preferably isocyanates or (activated) amines, most preferably isocyanates.

The Polymer Backbone P

The polymer backbone P has a molecular weight of 250 to 200,000, preferably 1000 to 100,000, more preferably 2000 to 80,000, more preferably 3000 to 50,000 and most preferably 5000 to 30,000 Dalton.

The polymer backbone P is preferably a hydrophilic polymer, and according to this invention, a hydrophilic polymer is defined as a polymer having a solubility in water of at least 1 g/L.

P may represent any type of polymer backbone known in the art, such as preferably polyethers, polyesters, polyamides, polyacrylates, polymethacrylates, polyolefins, hydrogenated polyolefins, polysiloxanes, polycarbonates, (per)fluorinated polyethers, polyvinylenes, or co-polymers of such polymers. More preferably, the polymer backbone is a polyether, polyester, polyacrylate, polymethacrylate, polyolefin, hydrogenated polyolefin, polycarbonate, polyvinylene, or a co-polymer of such polymers. Even more preferred are polyethers, polyesters, or copolymers thereof. Most preferably, P is a polyether, preferably a polyglycol, preferably a polyethylene glycol or a poly ethylene-co-propylene glycol (random or block), most preferably a polyethylene glycol.

Although some of the above listed polymer backbones P themselves may not be hydrophilic per se, co-polymerizing them with the right amount of water soluble polymer, or use of a combination of these polymer backbones P can lead to a water gellant, as will be obvious to a person skilled in the art.

The polymers P that are used to prepare the water gellant of this invention can have different functional groups, such as for example alcohols, amines, thiols, isocyanates, carboxylic acids or combinations of these end groups. Preferably, the functional groups are alcohols or amines, most preferably alcohols, preferably primary alcohols. In this preferred case, the polymer backbone P is derived from a hydroxy functional polymer $P—(OH)_n$.

The functional polymer P that is used to prepare the water gellant of this invention can have different numbers (n) of functional groups. The average functionality n of the functional polymer is preferably 1.8 to 10, more preferably 1.8 to 5, even more preferably 1.8 to 3, and most preferably 1.8 to 2.

The polymers P that are used to prepare the water gellant of this invention can be combinations of polymers with different backbone compositions, different architectures, different molecular weights and/or a different (numbers of) functional groups. For example, one can use a telechelic polyethylene glycol with a molecular weight of 5000 Dalton in combination with a telechelic polyester with a molecular weight of 500 Dalton.

According to the first embodiment of this invention, the functional polymer P that is used to prepare the water gellant is a telechelic polymer, and this telechelic polymer is preferably hydroxy functional. One can represent this telechelic polymer as $P—(OH)_n$, with n (about)$_2$, or 1.8 to 2, more preferably 1.9 to 2, most preferably 1.95 to 2. The polymer $P—(OH)_2$ is preferably selected from the group consisting of polyethers, polyesters, polyamides, polycarbonates, polysiloxanes, hydrogenated polyolefins, polyortho esters, or lower molecular weight materials that are derived from dimerized fatty acids, such as Pripol and Priplast, both marketed by Uniqema BV, the Netherlands, more preferably, the prepolymer backbone P is selected from the group consisting of polyethers or polyesters, most preferably P is selected from polyethers, most preferably polyethylene glycols.

Examples of telechelic functional polymers $P—(OH)_2$ are (a) polyetherdiols having a polyoxyalkylene structure, such as polyethylene glycols, polypropylene glycols, poly(ethylene-co-propylene) glycols (random or block), poly(ethylene-block-propylene-block-ethylene) glycols (also known as Pluronics), polytetramethylene glycols (i.e. polytetrahydrofurans) or poly(ethylene-co-tetramethylene) glycols. Other examples are (b) polyesterdiols or copolyester diols, made by polycondensation of dicarboxylic acids and diols, or by polycondensation of hydroxyacids, or by ringopening polymerisation of e.g. ∈-caprolactone, glycolide, lactide, δ-valerolactone, 1,4-dioxane-2-one, 1,5-dioxepan-2-one, oxepan-2,7-dione, and the like. Specific examples are poly ∈-caprolactonediols, hydroxy terminated polyadipates or polyglutarates, such as hydroxy terminated poly(1,4-butylene adipate)s, hydroxy terminated poly(1,2-ethylene adipate)s, hydroxy terminated poly(1,4-butylene glutarate)s, hydroxy terminated poly(2-methyl-1,3-propylene adipate)s, hydroxy terminated poly(2-methyl-1,3-propylene glutarate)s, hydroxy terminated poly(2-methyl-1,5-pentylene adipate)s, polyesterdiols of polylactides, polyglycolides, poly(lactide-co-glycolide)s, poly(hydroxy butyrate)s, polyterephthalates such as polyethyleneterephthalates and polybutyleneterephthalates, polyisophthalates (e.g. hydroxy terminated copolymers of 5-NaSO$_3$-isophtalic acid, isophthalic acid, diethyleneglycol and bis-hydroxymethylene-cyclohexane, hydroxy terminated copolymers of isophtalic acid and 1,4-butanediol, hydroxy terminated copolymers of 5-NaSO$_3$-isophthalic acid, adipic acid, phthalic acid and 1,6-hexanediol) and polyphthalates such as poly(1,6-hexylene phthalate)s or hydroxy terminated copolymers of phthalic acid and diethyleneglycol. Further examples include (c) polyolefine diols or hydrogenated polyolefine diols, such as hydroxyl functionalized polybutadienes or hydroxyl functionalized hydrogenated poly(ethylene-butylene)s such as Kraton L-2203 or Nisso-type materials. Other examples are (d) hydroxy functionalized polycarbonates and co-polycarbonates based on glycols or made by ring opening polymerization of e.g. trimethylenecarbonate, 1,3-dioxepane-2-one, 1,3-dioxanone-2-on and 1,3,8,10-tetraoxacyclotetradecane-2,9-dione. Examples are hydroxy terminated poly(1,3-propanediol carbonate)glycols, poly(trimethylenecarbonate)s, poly(1,6-hexanediol carbonate)glycols. More examples include (e) low molecular weight diols based on dimerized fatty acids such as Pripols and Priplasts, such as Pripol 2033, Priplast 3190 or Priplast 3192 (marketed by Uniqema BV, the Netherlands), (f) polysiloxanes such as α,ω-bis(6-hydroxyhexyl)polydimethylsiloxanes, α,ω-bis(oligo-ethyleneoxide) polydimethylsiloxanes, and (g) polyamides such as α,ω-dihydroxy-polyamides. Of course, examples are also (h) alcohol terminated co-polymers of the examples mentioned above, such as (block)-co-polymers of poly-caprolactone and ethylene glycol or (block)-co-polymers of poly-caprolactone and tetramethylene glycol. Preferred examples of hydroxy functional telechelics P—(OH)$_2$ are those of categories (a) and (b), more preferred are those of (a). Within category (a), the polymer P—(OH)$_2$ is preferably selected from the group consisting of polyethylene glycol, poly(tetrahydrofuran) or poly(ethylene-co-propylene) glycol (random or block). Most preferably, the polymer within category (a) is polyethylene glycol.

As an alternative, although less preferred, telechelic polyoxyalkylene amines may be used, such as polyethylene glycols or poly(ethylene-co-propylene) glycols with terminal amino groups. Examples are Jeffamines® as sold by Huntsman.

According to the second embodiment of this invention, the functional polymer P that is used to prepare the water gellant is selected from the group consisting of multifunctional polymers, functional star polymers, functional grafted polymers, functional (hyper)branched polymers and functional dendritic polymers. More preferably, in this embodiment, the functional polymer is a functional star polymer, a functional grafted polymer or a functional branched polymer, most preferably a functional star polymer. Also in this embodiment, the functional polymers are preferably hydroxy functional, and can then be represented by P—(OH)$_n$ with n>2.

Functional star polymers P—(OH)$_n$ are preferably polyethers or polyesters, more preferably polyethers. Polyester star polymers are preferably preparable by ring opening polymerization of suitable monomers such as lactones (e.g. ∈-caprolactone, lactides, glycolides, and the like), using a multifunctional alcohol initiator, such as glycerol, erythritol, 1,1,1-tris(hydroxymethyl)ethane, 1,1,1-tris(hydroxymethyl)propane, pentaerythritol, saccharoses, and derivatives thereof. A specific polyester star polymer is a polycaprolactone triol prepared from a 1,1,1-tris(hydroxymethyl)propane core. Polyether star polymers are preferably obtainable by polymerizing ethylene oxide, propylene oxide or a mixture thereof, using a multifunctional initiator as core molecule. Poly(ethylene glycol) star polymers having OH functional groups can for example be prepared by living anionic polymerization using divinyl benzene as the core molecule, whereafter the polyethylene oxide arms are grown outwards from the core. Other methods include the use of dendritic core molecules having a multitude of reactive groups from which polyethylene oxide arms can grow in outward direction. More simple initiators, e.g. glycerol, erythritol, 1,1,1-tris(hydroxymethyl)ethane, 1,1,1-tris(hydroxymethyl)propane, pentaerythritol, saccharoses, and derivatives thereof, can be used as well as core molecule. Most preferably, the functional star polymer is a poly(ethylene oxide) polymer having OH end-groups according to Formula (8):

$$Z—[(CH_2CH_2O)_r—OH]_s \quad \text{Formula (8)}$$

wherein Z represents the multifunctional core, r is in the range of 4 to 250 and s is in the range of 3 to 10, more preferably s is in the range of 3 to 5, and most preferably s is (about) 3.

Examples of functional hyperbranched polymers having OH-groups are Hybrane® from DSM, The Netherlands, and Boltorn® from Perstorp, Sweden. Examples of branched polymers are branched polyglycerols or branched polyesters having OH-groups. Branched polyglycerols having OH end-groups can for example be obtained by Lewis acid catalyzed polymerization of glycidol. Branched polyesters can for example be prepared by polymerizing a dicarboxylic acid and/or a dicarboxylic anhydride, a diol such as polyethylene glycol and a multifunctional alcohol having at least three OH groups, e.g. trimethylol propane or glycerol. A specific example of a branched polyester is a trifunctional poly(2-methyl-1,3-propylene)adipate.

Functional grafted polymers P—(OH)$_n$ are obtainable by (co)polymerization of vinyl monomers. Preferably, these vinyl monomers are selected from the group consisting of:

(a) acrylate or methacrylate monomers according to Formula (9),

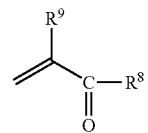

Formula (9)

wherein R$^8$ is independently selected from the group consisting of:
(i) OH;
(ii) C$_1$-C$_{12}$ linear or branched alkoxy, optionally substituted with 1-6 hydroxy groups;
(iii) amide according to the formula —N(R$^{10}$)$_2$ wherein R$^{10}$ can be hydrogen or C$_1$-C$_6$ linear or branched alkyl, optionally substituted with 1-6 hydroxy groups;
(iv) ammonium salt according to the formula —[N(R$^{10}$)$_3$]$^+$ X$^-$, wherein R$^{10}$ is as defined for (iii) and X is a halogen atom; and
(v) a group according to the Formula (10)

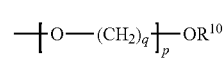

Formula (10)

wherein R$^{10}$ is as defined for (iii) and p is 1-50 and q=2 or 3 and where (CH$_2$)$_q$ can be linear or branched; and wherein R$^9$ is hydrogen or methyl;
(b) C$_1$-C$_{12}$ linear or branched alkyl vinyl ether;
(c) vinyl alcohol;
(d) C$_2$-C$_{12}$ α-alkenylene ω-sulfonate having an alkaline earth metal cation or an alkali metal cation;
(e) C$_7$-C$_{12}$ vinylaryl sulfonate according to Formula (11)

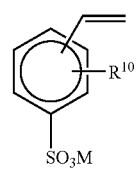

Formula (11)

wherein $R^{10}$ is as defined for (iii) and M is an alkaline earth metal or an alkali metal cation;

(f) $CH_2=CH-R^{11}$, wherein $R^{11}$ is selected from the group consisting of pyrrolyl, imidazolyl, pyrazolyl, pyridinyl, pyrazinyl, pyrimidinyl, pyrrolidyl, indolyl, indolizinyl, indazolyl, purinyl, quinolizinyl, quinolinyl, isoquinolinyl, phthalizinyl, naphtypyridinyl, quinoxalinyl, quinazolinyl, cinnolinyl, pteridinyl, pyrrolidonyl, pyrrolinyl, pyrrolidinyl, imidazolidinyl, imidazolinyl, pyrazolidinyl, pyrazolinyl, piperidyl, piperazinyl, indolinyl, isoindolinyl, morpholinyl, isoxazolyl, furazinyl, and isothiazolyl;

(g) $CH_2=CH-O-C(O)R^{12}$, wherein $R^{12}$ is selected from the group consisting of $C_1$-$C_6$ linear or branched alkyl;

(h) $CH_2=CH-CH_2OR^{13}$, wherein $R^{13}$ is selected from the group consisting of hydrogen and $C_1$-$C_6$ linear or branched alkyl; and (i) N-vinyl lactams according to the Formula (12)

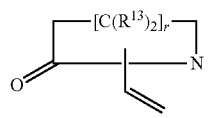

Formula (12)

wherein $R^{13}$ is as defined for (h) and r is 2-6.

More preferably, grafted polymers P—$(OH)_n$ are obtainable by co-polymerizations of monomers selected from groups (a) and (c), optionally co-polymerised with monomers of groups (b), (d)-(i). Most preferably, the monomers are selected from group (a), where preferably hydroxyethyl methacrylate (HEMA) or hydroxyethyl acrylate (HEA) are used as co-monomer.

Examples of functional dendritic polymers are poly(propylene imine) dendrimers, poly(amido amino) dendrimers (both these have amine end groups), or arborol type dendrimers that are alcohol terminated dendrimers.

The multifunctional polymer P according to the second embodiment of the invention can be of natural origin or of synthetic origin. However, according to the invention, it is preferred that the polymer is of synthetic origin, and many examples are given above. If the polymer is of natural origin, it is preferred that it is selected from the group consisting of proteins, e.g. proteins selected from the group consisting of collagen, gelatine, or fibrin, and polysaccharides, e.g. polysaccharides selected from the group consisting of hyaluronate, agar, agarose, xantham gums, natural gum, alginate, chitosan or insulin, or synthetic derivatives from them, preferably collagen or chitosan.

The Hydrophobic Linker L and its Introduction into the Water Gellant

The Hydrophobic Linker L

The hydrophobic linker L between the polymer backbone P and the 4H-unit is selected from the group consisting of cyclic, linear or branched $C_2$-$C_{24}$ alkylene groups, $C_6$-$C_{24}$ arylene groups, $C_7$-$C_{24}$ alkarylene groups and $C_7$-$C_{24}$ arylalkylene groups, wherein the alkylene groups, arylene groups, alkarylene groups and arylalkylene groups optionally, but not preferably, comprise 1-5 heteroatoms selected from the group consisting of oxygen, nitrogen and sulphur.

More preferably, the hydrophobic linker L is selected from the group consisting of cyclic, linear or branched $C_4$-$C_{20}$ alkylene groups and $C_6$-$C_{20}$ arylene groups, wherein the alkylene groups or arylene groups optionally, but not preferably, comprise 1-3 heteroatoms, preferably oxygen. Even more preferably, L is selected from the group consisting of cyclic, linear or branched $C_6$-$C_{20}$ alkylene groups. Most preferably, L is selected from cyclic, linear or branched $C_6$-$C_{12}$ alkylene groups.

The linker L may also be perfluorinated or partly fluorinated versions of the linkers described above, but this is not preferred.

Introduction of the linker L into the Water Gellant of this Invention

The hydrophobic linker L can be introduced into the water gellant by two methods: (a) the linker L is covalently attached to the polymer backbone P and the resulting functional prepolymer is connected to a 4H-unit building block to produce the water gellant or (b) the linker L is attached to the 4H-unit and the resulting building block is covalently attached to the polymer backbone P to produce the water gellant. Method (a) is preferred and is described here in detail.

The hydrophobic linker L can be covalently connected to the polymer backbone P using any reaction or sequence of reactions known in the art. Type of reactions may include coupling reactions such as for example etherifications, esterifications, amidation reactions, carbamate forming reactions or Michael-type additions, in which cases P and L are connected via ether, ester, amide, urethane or amine moieties, respectively. Other type of reactions that may be involved in the introduction of the linker L are protection or deprotection reactions and activation reactions, as will be appreciated by persons skilled in the art.

Preferably, in synthetic method (a), functional polymers P—that are preferably hydroxy functional polymers P—$(OH)_n$—are converted in a two step procedure to give prepolymers with functional hydrophobic linker groups L attached to them. The first step involves the activation of a functional polymer with a (thio)carbonyl-containing reactant to acquire an activated polymer, and the second step involves reaction of the activated polymer with (an excess of) a difunctional compound containing the hydrophobic linker L. The difunctional compound can be any difunctional compound having at least one nucleophilic group, such as a diamine, a diol, an amino-alcohol, a dithiol, an amino acid or the like. Preferably, the difunctional compound is a diamine, so that amine functional prepolymers are prepared.

For the preferred case where the starting polymer P is hydroxy functional and where the difunctional compound is a diamine, the two reaction steps are given by Reactions (i) and (ii):

Reaction (i)

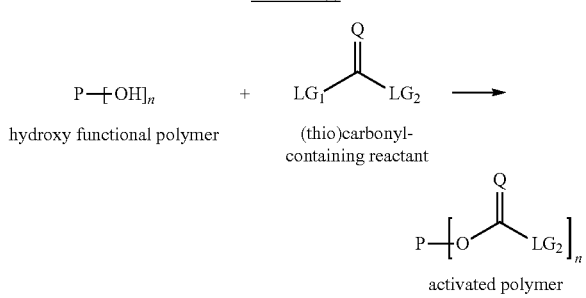

Reaction (ii)

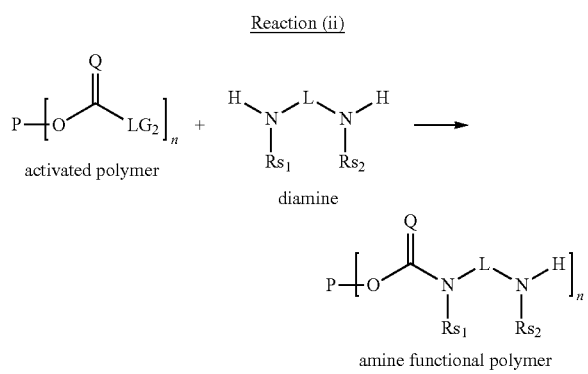

wherein P is the polymer backbone, L is the hydrophobic linker, and n is the (average) functionality of the hydroxy functional polymer and all three are defined as above, where Q is an oxygen or a sulphur atom, preferably an oxygen atom, where $Rs_1$ and $Rs_2$ are residues that are related to the used diamine and may represent independently any residue known in the art, such as hydrogen or $C_1$-$C_6$ alkyl groups, so that $Rs_1$ and $Rs_2$ may provide extra hydrophobicity to the spacer between the polymer backbone P and the 4H-unit, and where $LG_1$ and $LG_2$ both independently represent a leaving group, and they may represent any leaving group known in the art, such as for example imidazoles, triazoles, halogens, N-hydroxysuccinimides, (substituted) phenols and carboxylates. $LG_1$ and $LG_2$ may be the same leaving group, for example, $LG_1$ and $LG_2$ may both be an imidazole group, so that in case of Q being an oxygen, the carbonyl-containing reactant is 1,1'-carbonyldiimidazole (CDI).

In the preferred embodiment of this invention where n is (about) 2, and where the functional polymer $P-(OH)_2$ is telechelic, Reactions (i) and (ii) translate into Reactions (iii) and (iv), that are given below, with P, Q, L, $Rs_1$, $Rs_2$, $LG_1$ and $LG_2$ being defined as above.

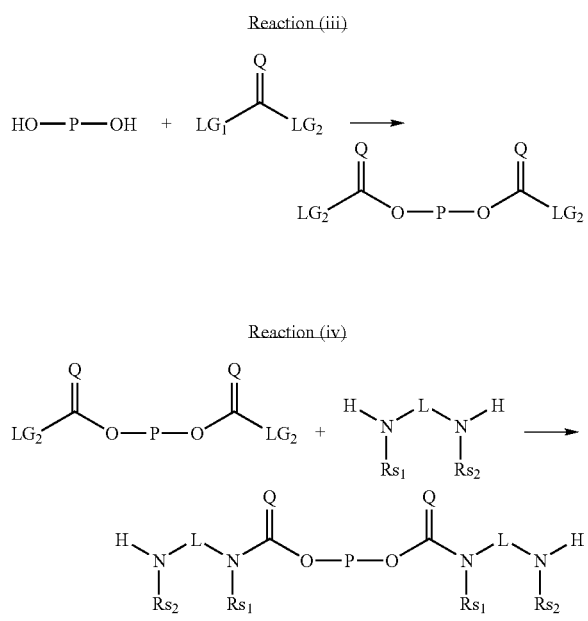

The applied synthetic methodology that is highlighted in Reactions (i) to (iv) is simple (e.g. no use of protective group chemistry), is versatile (i.e. able to produce many types of amine end groups with incorporated linkers L on a broad range of polymer backbones P), does not require metal catalysts for coupling reactions, circumvents the use of isocyanate chemistry and/or the use of metal hydrogenation catalysts that are routinely applied in the synthesis of amine functional polymers, can produce stable multifunctional polymeric materials with a high degree of definition (i.e. the amine functionality is high), and allows for upscaling using quality control conditions. Therefore, according to a very preferred embodiment of the present invention, the water gellant is prepared using the described synthetic method wherein in a first step a telechelic functional polymer $P-(OH)_2$ is reacted with a carbonyl compound of the formula $LG_1$-C(O)-$LG_2$, wherein $LG_1$, $LG_2$ and Q are as defined above, to form a functionalised prepolymer intermediate, and wherein in a second step the functionalised prepolymer intermediate is reacted with a diamine $H(R_{S1})N$-L-$N(R_{S2})H$.

Specifications to the Reactions (i) to (iv)

$LG_1$ and $LG_2$ in the (thio)carbonyl containing reactant that is used in Reactions (i) and (iii) both represent a leaving group. Leaving groups $LG_1$ and $LG_2$ can be any leaving group known in the art, and can for example and preferably be imidazole or a derivative thereof, triazole or a derivative thereof, a halogen, N-hydroxysuccinimide or a derivative thereof, a (substituted) phenol, a (substituted) thiophenol, a thiol, certain alcohols (e.g. 1,1,1-trichloro methanol, 2-halo, 2,2-dihalo alcohols, 2,2,2-trihalo or 2-methylsulfonyl ethanol, or (substituted) benzyl alcohols), a carboxyl derivative, an amide (e.g. ∈-caprolactam), a tosylate, a mesylate and a triflate. More preferably, the leaving group is imidazole or triazole or derivatives thereof, chloride, trichloromethanol, N-hydroxysuccinimide or a derivative thereof, or a (substituted) phenol. More preferably, the leaving group is an imidazole, a N-hydroxysuccinimide, a (substituted) phenol or a chloride. Even more preferred are imidazole or N-hydroxysuccinimide; most preferred is imidazole.

Note that, for convenience reasons only, leaving groups are mentioned interchangeably in this application as acids (phenol and not phenolate; imidazole and not imidazolyl anion) or as bases (chloride and not hydrochloride).

In one embodiment of this invention, $LG_1$ and $LG_2$ are the same leaving group and preferred examples of the (thio) carbonyl containing reactants are then 1,1'-carbonyldiimidazole, 1,1'-carbonylbis(2-methylimidazole), 1,1'-carbonylbis(benzo-triazole), 1,1'-carbonyl-di-(1,2,4-triazole), N,N'-disuccinimidyl carbonate, diphenyl carbonate, di-para-nitrophenyl carbonate, di-pentafluorophenyl carbonate, di-2,3,5,6-tetrafluorophenyl carbonate, di-methylphenyl carbonates, di-methoxyphenyl carbonates, triphosgene, phosgene, thiophosgene, 1,1'-thiocarbonyldiimidazole, and the like. More preferred examples are 1,1'-carbonyldiimidazole, N,N'-disuccinimidyl carbonate, diphenyl carbonate, di-para-nitrophenyl carbonate, di-pentafluorophenyl carbonate, and di-para-methylphenyl carbonate. Even more preferred are 1,1'-carbonyldiimidazole and N,N'-disuccinimidyl carbonate, most preferred is 1,1'-carbonyldiimidazole.

In another embodiment of this invention, $LG_1$ and $LG_2$ are different leaving groups, so that the reactant is a-symmetrical. In this case, $LG_1$ is preferably a halogen or N-hydroxysuccinimide, most preferably a chloride. Additionally, $LG_2$ is preferably a (substituted) phenol or an alcohol such as 2-halo, 2,2-dihalo, 2,2,2-trihalo, 2-methylsulfonyl alcohols, or (substituted) benzyl alcohols. More preferably, $LG_2$ is a (substituted) phenol such as preferably phenol, (ortho, para or metha) halo-, methoxy- or nitro-phenol, most preferably $LG_2$ is phenol. In this embodiment, specific examples of (thio)

carbonyl containing reactants are therefore chloroformates, such as (substituted) phenyl chloroformates, (substituted) benzyl chloroformates or 2,2,2-trichloroethyl chloroformate, or N-succinimidyl carbonates such as N-succinimidyl-2,2,2-trichloroethyl carbonate, N-(benzyloxycarbonyloxy)-succinimide and 2-(methylsulfonyl)-ethyl-N-succinimidyl carbonate. More preferred examples are (substituted) phenyl chloroformates, most preferably phenyl-chloroformate.

In another less preferred and specific embodiment of this invention, the (thio)carbonyl containing reactant is not a (thio)carbonate derivative, as those mentioned above, but is an oxalic acid derivative. Examples are oxalylhalides such as oxalyl chloride, N,N'-disuccinimidyl oxalate, 1,1'-oxalyldi-imidazole, (sulfosuccinimidyl)oxalate sodium salt, di(1-benzotriazolyl)oxalate and di((substituted) phenyl)oxalates.

The diamine that is used in Reactions (ii) and (iv) can be any diamine known in the art. L is defined as above and $Rs_1$ and $Rs_2$ are residues that are independently selected from the group consisting of hydrogen, cyclic, linear or branched $C_1$-$C_{20}$ alkyl groups, $C_6$-$C_{20}$ aryl groups, $C_7$-$C_{20}$ alkaryl groups and $C_7$-$C_{20}$ arylalkyl groups, wherein the alkyl groups, aryl groups, alkaryl groups and arylalkyl groups optionally comprise 1-5 heteroatoms selected from the group consisting of oxygen, nitrogen and sulphur, and where $Rs_1$ and $Rs_2$ may optionally be linked with each other, thereby forming a cyclic alkylene, arylene, alkarylene or arylalkylene structure. More preferably, $Rs_1$ and $Rs_2$ are residues that are independently selected from the group consisting of hydrogen, cyclic, linear or branched $C_1$-$C_{12}$ alkyl groups, and $C_6$-$C_{12}$ aryl groups, wherein the alkyl groups or the aryl groups optionally comprise 1-3 oxygens, and where $Rs_1$ and $Rs_2$ may optionally be linked with each other, thereby forming a cyclic alkylene or arylene structure. Even more preferably, $Rs_1$ and $Rs_2$ are independently selected from hydrogen, and linear or branched $C_1$-$C_6$ alkyl groups, where $Rs_1$ and $Rs_2$ may optionally be linked with each other thereby forming a cyclic alkylene structure. More preferably, $Rs_1$ and $Rs_2$ are independently selected from hydrogen and linear or branched $C_1$-$C_4$ alkyl groups, most preferably $Rs_1$ and $Rs_2$ are hydrogens.

According to the above, the diamine may have two primary amine groups ($Rs_1$ and $Rs_2$ are hydrogen), two secondary amine groups ($Rs_1$ and $Rs_2$ are not hydrogen) or one primary amine group and one secondary amine group (either $Rs_1$ or $Rs_2$ is a hydrogen). Primary amines are preferred due to their higher reactivity.

Examples of diamines used in Reactions (ii) and (iv) comprise—but are not limited to—alkylene primary diamines such as 1,4-diaminobutane, 1,6-diaminohexane, 1,8-diaminooctane, 1,10-diaminodecane, 1,12-diaminododecane, 2,2'-oxydiethylamine, isophorone diamine, 1,8-diamino-p-menthane, 2,2,4-(2,4,4)-trimethyl-1,6-hexanediamine, 4,4'-methylene-bis(cyclohexyl amine) and lysine or derivatives thereof, such as acid protected lysines, secondary diamines such as piperazine, 2-methyl piperazine, 2,6-dimethylpiperzine, N,N'-dimethyl-1,6-hexanediamine, N,N'-dibutyl-1,6-hexanediamine and 4,4'-bipiperidine, diamines with a primary amine and secondary amine group such as N-alkyl-1,6-diaminohexanes or 2-amino-pyrrolidine or 3-amino-piperidine, aromatic diamines such as metha- and para-diaminobenzenes, metha- and para-diaminotoluenes, metha- and para-aminobenzylamines. Preferred diamines are alkylene diamines with more than 3, preferably more than 5 carbon atoms in their constitution (i.e. more hydrophobicity is introduced), such as 1,4-diaminobutane, 1,6-diaminohexane, 1,8-diaminooctane, 1,10-diaminodecane, 1,12-diaminododecane, isophorone diamine, 1,8-diamino-p-menthane, 2,2,4-(2,4,4)-trimethyl-1,6-hexanediamine, 4,4'-methylene-bis(cyclohexyl amine), lysine and derivatives thereof, N,N'-dimethyl-1,6-hexanediamine and 4,4'-bipiperidine. More preferred diamines are 1,6-diaminohexane, 1,10-diaminodecane, 1,12-diaminododecane and isophorone diamine. Even more preferred examples are 1,12-diaminododecane and 1,6-diaminohexane. Most preferred example is 1,6-diaminohexane.

Specifically, 1,2-diamino-arylenes, 1,2-ethylenediamines ($L=C_2$) and 1,3-propylenediamines ($L=C_3$) are less preferred, as these diamines lead to prepolymers with a lesser stability.

Reactions (i) and (iii) can be executed in the bulk or in solution, preferably in concentrated solution (molar concentration of the (thio)carbonyl containing reactant in the reaction mixture is higher than 0.1 M, preferably higher than 0.3 M, most preferably higher than 0.5 M). Reaction solvents are preferably aprotic solvents known in the art, such as ethers, such as diethyl ether, THF, methyl-tetrahydrofuran, dioxane and methyl-tert-butyl ether, DMSO, dimethyl acetamide, NMP, chloroform, dichloromethane, ketones such as acetone, MEK and methyl-tert-butyl ketone, esters such as ethyl acetate and butyl acetate, toluene, alkanes such as cyclohexane, pentane, hexane and isododecane, and cyclomethicones such as D5.

Reaction (i) and (iii) are preferably executed at temperatures lower than 130° C., more preferably lower than 70° C., most preferably lower than 40° C.

The hydroxy functional polymer $P$—$(OH)_n$ is preferably used dry or dried, i.e. containing no or little water. Preferably, the reaction is executed under an inert atmosphere of nitrogen or argon.

The (thio)carbonyl containing reactant is preferably used in molar excess when compared to the moles of hydroxy groups in the reactant $P$—$(OH)_n$. Preferably, the molar excess is higher than 1.2-fold, more preferably, higher than 1.5-fold, most preferably higher than 2-fold. In case $LG_2$ is different than $LG_1$, the (thio)carbonyl containing reactant is preferably used in slight molar excess. Preferably, the molar excess is lower than 1.5-fold, more preferably, lower than 1.25-fold, most preferably lower than 1.1-fold. In case chloroformates are used as (thio)carbonyl containing reactants ($LG_1$=Cl), a base is used to scavenge the formed HCl (i.e. $H.LG_1$). Preferred examples of such bases are pyridines and tertiary amines such as triethylamine or other trialkylamines.

The activated polymer can be isolated by different type of work-up procedures that are known in the art such as precipitation, extraction, washing, drying, filtration and evaporation procedures, or combinations thereof. Before work-up, the excess of (thio)carbonyl containing reactant may be eliminated. Elimination of the (thio)carbonyl containing reactant can be done by reaction with water or with an alcohol, preferably a secondary alcohol such as for example isopropanol or 2,3-butanediol. Most preferably elimination is done with water. Finally, the reaction mixture of reaction (i) or (iii) can be used in the next reaction step (ii) or (iv) without work-up, preferably after elimination of the excess of (thio)carbonyl containing reactant.

Reactions (ii) and (iv) can be executed in the bulk or in solution, preferably in concentrated solution (molar concentration of the diamine reactant in the reaction mixture is higher than 0.1 M, preferably higher than 0.3 M, most preferably higher than 0.5 M). Reaction solvents are preferably aprotic solvents known in the art, such as ethers, such as diethyl ether, THF, methyl-tetrahydrofuran, dioxane and methyl-tert-butyl ether, DMSO, dimethyl acetamide, NMP, chloroform, dichloromethane, toluene, alkanes such as cyclohexane, pentane, hexane and isododecane, and cyclomethicones such as D5. Esters such as ethyl acetate and butyl acetate are less preferred; ketones such as acetone, MEK and methyl-tert-butyl ketone are even less preferred.

Reactions (ii) and (iv) are preferably executed at temperatures lower than 130° C., more preferably lower than 70° C., most preferably lower than 40° C.

The diamine is preferably used in molar excess when compared to the moles of activated species O—C(Q)-$LG_2$ in the activated polymer reactant. Preferably, the molar excess of diamine is higher than 1.5-fold, more preferably, higher than 2-fold, most preferably higher than 3-fold. Importantly, in reactions (ii) and (iv), the activated polymer is preferably added in portions to the excess of diamine. This can for example be done by drop wise addition of a solution of the activated polymer to a solution of the diamine.

The amine functional polymer can be isolated by different type of work-up procedures that are known in the art such as precipitation, extraction, washing, drying, filtration and evaporation procedures, or combinations thereof. For some low-volatile diamines such as piperazine or 1,3-propylene amine, the excess of diamine can be removed by evaporation.

The amine functional polymers as prepared in Reactions (ii) and (iv) preferably have a high degree of definition meaning that, (a) on average at least 65% of the alcohol groups in the alcohol functional polymer P—$(OH)_n$ precursors are converted into amine groups, more preferably at least 75%, most preferably at least 85%, and that (b) on average at least 80% of all functional end groups in the amine functional polymer are indeed amine groups, more preferably more than 90%, most preferably more than 95%, and that (c) the average number molecular weight of the amine functional polymer does not exceed by more than 50% the summation of the number molecular weight of the alcohol functional polymer P—$(OH)_n$ plus n times the molecular weight of the diamine, more preferably by more than 40%, most preferably by more than 30%.

The Hydrogel

In an embodiment of this invention, the water gellant comprises biodegradable moieties, that may be single bonds (e.g. an ester bond) or linkages or may be regions with multiple biodegradable bonds (e.g. a polyester or oligoester). The moieties may occur within parts of the polymer backbone P, in the linker L, in the 4H-units, and/or in the attachments between the polymer P and the linker L, or the attachments between the linker L and the 4H-units. Examples of biodegradable bonds or linkages are covalent ester, ortho-ester, ortho-ester, urethane, thio-urethane or amide bonds, but are preferably ester bonds.

The amount of the water gellant in the hydrogel ranges from 0.3%-50.0% by weight, preferably from 1%-25% by weight, more preferably from 1%-15% by weight, more preferably from 1%-8% by weight, and most preferably from 1%-3.4% by weight, based on the total weight of the hydrogel. The hydrogel may contain additional functional ingredients that will contribute to the specific use of the hydrogel.

The hydrogel comprises 50.0 to 99.7 wt. % of water, preferably 60 to 99 wt. %, and most preferably 80 to 98 wt. %, based on the total weight of the hydrogel.

Obviously, but not preferably, the hydrogel may contain other polar solvents, preferably those solvents having a dielectric constant $\in$ at 20° C. of at least about 20. The upper limit is given by the dielectric constant $\in$ at 20° C. for pure water which is about 80 (Handbook of Chemistry & Physics, $59^{th}$ Ed., page E-61, 1978-1979). Suitable examples are DMSO, alcohols, preferably ethanol and glycols, but more preferably ethanol and ketones, such as acetone. Preferably, the amount of other solvents is lower than 15% by weight, more preferably lower than 8% by weight, and most preferably lower than 2% by weight, calculated on the basis of the total weight of the hydrogel.

The hydrogels according to the present invention have a wide range of mechanical properties, ranging from elastic to tough, depending on the nature of the polymer backbone P, the nature of the linker L, and the number of 4H-units attached to the polymer. In the preferred case of elastic hydrogels, the hydrogel materials preferably display an elongation at break at 25° C. greater than about 5%, more preferably greater than 20%, more preferably greater than 100%.

The reversible cross-links in the hydrogel allow for switching the gel into a liquid by the application of heat, changing the nature of the solvent or the concentration of the water gellant. Consequently, the processing or administration of the hydrogel can be done with processes known for liquids, like spraying or pumping. Preferably, the polymers present in the hydrogel have a relatively low number average molecular weight, preferably in the range from 1200 to 100000, more preferably from 2000 to 50000, most preferably from 7500 to 21000, in order to allow for easy solution processing of the water gellant, such as pumping or spraying.

The hydrogels can for example be used in pharmaceutical applications or biomedical applications such as controlled drug-delivery, tissue engineering, wound-dressings and wound-care, artificial articular cartilage material, soft contact lenses, tissue-adhesion, lubricating coatings for medical devices, as superabsorbers, and as thickeners for aqueous solvents.

The hydrogels according to the present invention can be prepared by three different methods: (i) the hydrogel can be dissolved in aqueous solvent at elevated temperatures between 40° C. and 95° C., preferably between 60° C. and 90° C., followed by cooling down to temperatures between 0° C. and 40° C., preferably between 20° C. and 40° C.; (ii) the hydrogel can be swelled in aqueous solvent at temperatures between 0° C. and 60° C., preferably between 20° C. and 40° C.; and (iii) the hydrogel can be dissolved or dispersed in any organic water-miscible solvent, such as for example THF, acetone, MEK, alcohols, such as ethanol, DMSO, NMP, or solvent mixture, followed by the addition of water and subsequently the optional removal of the organic solvent with evaporation in vacuo or removal of the organic solvent by washing with water.

The hydrogels are applied in their gelled form after gelling the aqueous solvent with water gellant in a mould, eventually followed by cutting of the gel, or the water gellants are applied in their liquid state followed by gelling the polymers to a hydrogel after administration of the effective amount of the polymer to the desired site.

Additional ingredients in the hydrogels can be antioxidants, preservatives, fillers, salts, pH-buffers, dyes, bone-extracts, or bioactive species.

In another preferred embodiment of this invention, the hydrogels are used in biomedical applications, such as carriers for the controlled release of drugs, scaffolds for tissue-engineering, or as adhesives or sealants for tissue. In these uses, the hydrogels also preferably comprise a biologically active or pharmaceutically active compound. The hydrogel may also comprise a bioactive species, e.g. a living cell, an enzyme, or a micro-organism. A living cell in this embodiment means and includes individual animal and plant cells, cell clusters, tissues, organs and organisms, including organisms such as bacteria, fungi or moulds. A biologically active or pharmaceutically active compound, as used herein, includes a compound which provides a therapeutic, diagnostic, or prophylactic effect, a compound that affects or participates in tissue growth, cell growth, cell differentiation, a compound that may be able to invoke a biological action such as an immune response, or could play any other role in one or more biological processes. Such compounds, peptide or non-peptide, protein or non-protein, include, but are not limited to, antimicrobial agents (including antibacterial, hemotherapeutic and anti-fungal agents), anti-viral agents, anti-tumor agents, hormones, hormone antagonistics, corticosteroids such as mineralocorticosteroids or glucocorticosteroids, androgents, estrogens, progestins immunogenic agents, anti-inflammatory agents, anti-gout agents, centrally acting analgesics, local anesthetics, centrally active muscle relaxants, growth factors, (fluorescent) dyes, contrast agents, nucleic acids, lipids, lipopolysaccharides, (poly)saccharides, vitamins, and peptides, polypeptides and proteins in general.

Apart from the previous list, it is also possible to load the hydrogel with inorganic compounds, such as reactive oxygen scavengers and bone-extracts like apatite.

It is possible within the scope of the present invention to incorporate drugs of a polymeric nature, but also to incorporate drugs or vitamins of a relatively small molecular weight of less than 1500, or even less than 500.

Additionally, two or more different biologically active compounds may be present in the hydrogel. This is especially beneficial when the bioactivity is based on multivalent and/or synergistic interactions. A non-limiting example of such interaction is that cell adhesion is advantageously mediated by a combination of RGD and PHSRN peptides.

EXAMPLES

The following examples further illustrate preferred embodiments of the invention. When not specifically mentioned, chemicals are obtained from Aldrich. The synthesis of 4H-unit building blocks, more specifically ureido pyrimidone (UPy) building blocks, is shown, as well as the synthesis of amine functional prepolymers with hydrophobic endgroups, and the synthesis of the water gellants. Finally, the hydrogels of this invention are introduced, by explaining their preparation and showing their properties.

Example 1

Preparation of UPy1

1,6-Hexyldiisocyanate (650 g) and methylisocytosine (or 2-amino-4-hydroxy-6-methyl-pyrimidine, 65.1 g) were suspended in a 2-liter flask. The mixture was stirred overnight at 100° C. under an argon atmosphere. After cooling to room temperature, a liter of pentane was added to the suspension, while stirring was continued. The product was filtered, washed with several portions of pentane and dried in vacuum. A white powder was obtained. $^1$H NMR (400 MHz, CDCl$_3$): δ 13.1 (1H), 11.8 (1H), 10.1 (1H), 5.8 (1H), 3.3 (4H), 2.1 (3H), 1.6 (4H), 1.4 (4H). FT-IR (neat): ν (cm$^{-1}$) 2935, 2281, 1698, 1668, 1582, 1524, 1256.

Example 2

Preparation of UPy2

2-Amino-4-hydroxy-5-(2-hydroxy ethyl)-6-methyl-pyrimidine (12 gram) was suspended in IPDI (150 mL) and was stirred overnight at 90° C. under an argon atmosphere. A clear solution developed. The solution was cooled and precipitated in hexane. The solid was filtered, stirred in another portion of hexane, and then the product was isolated by filtration, washing with hexane and drying of the residue. Yield: 98%. $^1$H NMR (400 MHz, CDCl$_3$): δ 13.1 (1H), 11.9 (1H), 10.2 (1H), 4.8-4.5 (1H), 4.2 (2H), 4.0-3.2 (3H), 3.1-2.9 (3H), 2.7 (2H), 2.3 (3H), 1.9-1.6 (4H), 1.4-0.8 (26H). FT-IR (neat): ν (cm$^{-1}$) 2954, 2254, 1690, 1664, 1637, 1590, 1532, 1461, 1364, 1307, 1257, 1034, 791. MALDI-TOF-MS, [M$^+$]=614, [M+Na$^+$]= 636.

Example 3

Preparation of UPy3

The building block UPy1 (46 g) was suspended in chloroform (1 L), and thereafter hydroxy ethyl acrylate (HEA, 36 mL) and 10 drops of dibutyl tin dilaurate (DBTDL) were added. The mixture was stirred at an oil bath temperature of 90° C. for 4 hours, and was then cooled and filtered. The filtrate was concentrated and an excess of diethylether was added. The white precipitate was collected by filtration, and was washed with diethylether. Drying in vacuo gave a white solid product. $^1$H NMR (400 MHz, CDCl$_3$): δ 13.1 (1H), 11.8 (1H), 10.1 (1H), 6.5 (1H), 6.2 (1H), 5.9 (2H), 5.1 (1H), 4.4 (4H), 3.3 (2H), 3.2 (2H), 2.1 (3H), 1.7-1.3 (8H). FT-IR (neat): ν 3307, 2928, 1725, 1702, 1682, 1664, 1584, 1548, 1258, 1192. This type of 4H-unit building block (or similar molecules with methacrylate, acrylamide or methacrylamide groups) can be reacted in Michael-type addition reactions with amine terminated polymers such as the ones given in Table 1 to give materials in which the linker L is coupled to the 4H-unit via secondary and/or tertiary amines.

Example 4

Preparation of UPy4

1,12-Diisocyanatododecane (4.5 g) and methylisocytosine (or 2-amino-4-hydroxy-6-methyl-pyrimidine, 0.37 g) were suspended in a 10 mL flask. The mixture was stirred overnight at 90° C. under an argon atmosphere. After cooling to room temperature, 2 mL of hexane was added to the suspension, while stirring was continued. The suspension was poured into 40 mL of hexane. The precipitated product was filtered, washed with several portions of hexane and dried in vacuum. A white powder was obtained. $^1$H NMR (300 MHz, CDCl$_3$): δ 13.1 (1H), 11.8 (1H), 10.1 (1H), 5.8 (1H), 3.3 (4H), 2.1 (3H), 1.6 (4H), 1.4 (16H). FT-IR (neat): ν (cm$^{-1}$) 2918, 2267, 1698, 1665, 1577, 1523, 1223.

Example 5

Preparation of UPy5, a 4H-Unit with Attached Linker L

UPy1 (0.55 g) in a 1:1 mixture of dry DMSO and chloroform (10 mL) is filtered and the filtrate is added in portions to isophorone diamine (2.3 g) that is stirred in dry DMSO (3 mL). During addition and for a further 2 hours, the mixture is kept at 40° C. under an argon atmosphere. Thereafter, the clear solution is cooled to room temperature and ethyl acetate (50 mL) is added to induce precipitation. The white product is filtered, washed with ethylacetate and dried. $^1$H NMR (400

MHz, DMSO-$d_6$): δ 9.7, 8.0-5.0 (broad), 6.0-5.4 (multiple signals), 4.0, 3.7, 3.2, 3.0, 2.7, 2.3, 2.1, 1.6-1.2, 1.2-0.6.

Example 6

Preparation of PEG2000-Diamine Prepolymer with n-$C_{10}$ Linker L

Reaction (i): To a solution of 1,1'-carbonyldiimidazole (CDI) (8.125 g, 40 mmol) in $CHCl_3$ (100 mL) was added over a period of 5 minutes a solution of dried telechelic hydroxy functional polyethylene glycol (PEG2000 diol, 10 g, 5 mmol, MW=2.0 kDalton) in $CHCl_3$ (100 mL). The reaction was executed under an argon atmosphere and was allowed to stir at room temperature for 24 hours. After concentration to a total volume of 100 mL via rotary evaporation, the solution was diluted slowly with diethyl ether until a total volume of ~600-800 mL was reached, resulting in precipitation of the activated polymer. This dilution-precipitation procedure was repeated to ensure complete removal of excess CDI prior to moving to the next reaction (ii). The CDI-activated material was moved directly into the next step to avoid possible hydrolysis of the end group.

Reaction (ii): To a solution of 1,10-diaminodecane (3.21 g, 18.6 mmol) in $CHCl_3$ (150 mL) was added slowly, over a one hour period, a solution of the CDI activated PEG-material as prepared in the first reaction (5 g, 2.3 mmol, MW=2.2 kD with activated endgroups) in $CHCl_3$ (75 mL). The reaction was allowed to stir overnight at room temperature under an argon atmosphere. After concentration of the solution to a volume of about 75 mL, diethyl ether was added slowly until a total volume of ~600-800 mL was reached, resulting in precipitation of the polymer. This dilution-precipitation procedure was repeated to ensure complete removal of excess diamine. $^1$H NMR (400 MHz, $CDCl_3$): δ 4.85 (2H), 4.2 (4H), 3.8-3.4 (EO-units), 3.15 (4H), 2.7 (4H), 2.0 (4H, br), 1.45 (8H), 1.25 (20H). This material can be denoted as 2K-10, where 2K stands for the PEG2000 polymer backbone and 10 stands for the n-decyl linker.

Examples 7

Preparation of Peg-Diamines with Incorporated Linkers L

Similar procedures to the one shown in example 6 have been followed for different molecular weights of hydroxy functional telechelic polyethylene glycols (PEGs 2 kD to 35 kD), for another hydroxy functional telechelic polymer (PCL1250, polycaprolactone) and for different diaminoalkanes. See Table 1 below for prepared materials and for a brief characterization of these materials.

TABLE 1

Prepared telechelic PEGs with amine functional linkers L as endgroups

| Example | PEG-polymer[a] | Diamine | L | Material |
|---|---|---|---|---|
| 2K-10 | PEG2000 | 1,10-diaminodecane | n-C10 | White stable powder |
| 2K-6 | PEG2000 | 1,6-diaminohexane | n-C6 | White stable powder |
| 3K-6 | PEG3000 | 1,6-diaminohexane | n-C6 | White stable powder |
| 3K-12 | PEG3000 | 1,12-diaminododecane | n-C12 | White stable powder |
| 6K-2 | PEG6000 | 1,2-diaminoethane | n-C2 | Unstable material |
| 6K-4 | PEG6000 | 1,4-diaminobutane | n-C4 | White stable powder |
| 6K-6 | PEG6000 | 1,6-diaminohexane | n-C6 | White stable powder |
| 6K-8 | PEG6000 | 1,8-diaminohexane | n-C8 | White stable powder |
| 6K-10 | PEG6000 | 1,10 diaminodecane | n-C10 | White stable powder |
| 6K-12 | PEG6000 | 1,12-diaminododecane | n-C12 | White stable powder |
| 10K-8 | PEG10000 | 1,8-diaminohexane | n-C8 | White stable powder |
| 10K-10 | PEG10000 | 1,10-diaminodecane | n-C10 | White stable powder |
| 10K-10c[b] | PEG10000 | isophorone diamine | cyclic and branched C10 | White stable powder |
| 10K-12 | PEG10000 | 1,12-Dodecanediamine | n-C12 | White stable powder |
| 20K-10 | PEG20000 | 1,10-diaminodecane | n-C10 | White stable powder |
| 20K-12 | PEG20000 | 1,12-diaminododecane | n-C12 | White stable powder |
| 35K-10 | PEG35000 | 1,10-diaminodecane | n-C10 | White stable powder |
| 35K-12 | PEG35000 | 1,12-diaminododecane | n-C12 | White stable powder |
| PCL-6[c] | PCL1250 | 1,6-diaminohexane | n-C6 | Wax |

[a]The number denotes the molecular weight of the PEG starting polymer.
[b]The reaction (ii) has been executed at about 60° C. in stead of room temperature.
[c]PCL-6 and its CDI-activated precursor was not isolated by precipitation in ether, but by extraction into chloroform using a brine water layer.

It is clear from the Table that all PEG-based materials are stable white powders, apart from the ethylene diamine end capped material 6K-2. Possibly, the end group forms cyclic ethylene urea, thereby reforming the alcohol end group.

NMR and MALDI-TOF-MS data for material 6K-6 are briefly discussed here to demonstrate the high definition of the prepared materials.

$^1$H NMR (400 MHz, $CDCl_3$): δ 4.85 (bs, 2H, C(O)NH), 4.2 (t, 4H, $CH_2OC(O)$), 3.8-3.4 (m, 541H, $CH_2O$), 3.15 (q, 4H, $CH_2NHC(O)$), 2.7 (t, 4H, $CH_2NH_2$), 2.0 (bs, 4H, $NH_2$), 1.45 and 1.25 (other $CH_2$-protons of the n-hexyl linker). The ratio of the integrals of the EO-units and the integrals of the hexyl linker is about 22, while theoretically this should be about 23. A deviation of only about 5% is observed. In $^{13}$C NMR ($CDCl_3$), the resonance at ca. 61 ppm of the carbons adjacent to the hydroxy group is gone after modification to the PEG-diamine product, proving conversion of the hydroxy functionalized PEG. In MALDI-TOF MS analysis, no significant signals of masses of ca. doubled molecular weight (12-13 kD) are found. Furthermore, and more importantly, observed masses around the expected molecular weight of 6000-7000 Dalton are $H^+$- and $Na^+$-adducts of the desired PEG-diamines with incorporated n-hexyl linkers, as an array of signals of m/z masses of 6491, 6535, 6579, 6623, etc. is recorded, as well as an array of signals of masses of 6469, 6513, 6557, 6601, etc, and no other array. The first array corresponds to $Na^+$-adducts, and the second array corresponds to $H^+$-adducts of oligomers of the desired PEG-diamines (for both given arrays, the number of EO-units is 140, 141, 142, 143, etc., respectively). This proves that the prepared material has the aimed-at telechelic structure with two aminohexyl end groups.

Example 8

Preparation of Telechelic Water Gellants with 4H-Units

UPy1 (585 mg; 2.0 equivalents) was added as a powder to a solution of pre-dried polyethylene glycol 10,000 terminated with aminododecyl groups (10.3 g; entry 10K-12 in Table 1) in CHCl$_3$ (50 mL). The reaction was allowed to stir overnight under an argon atmosphere at an oil bath temperature of 70° C. After cooling down to room temperature, ethanol was added (100 mL), and the hazy mixture was filtered over celite. The clear filtrate was concentrated by vacuum evaporation, and was diluted with ether under stirring. A white precipitate formed, and the mixture was stirred for 20 mins, then allowed to settle prior to filtration and washing with excess ether. The product was vacuum dried to give a white powder (95% yield). $^1$H NMR (400 MHz, CDCl$_3$): δ 13.1 (2H), 11.8 (2H), 10.1 (2H), 5.8 (2H), 4.9 (2H), 4.7 (2H), 4.5 (2H), 4.2 (4H), 3.8-3.3 (EO-units), 3.3 (4H), 3.1 (12H), 2.2 (6H), 1.6-1.1 (56H).

The powder and distilled water were added to a vial (10% gellant loading) and mixed with vigorous stirring at ca. 55-60° C. for 1 to 2 hours. The polymer solution was removed from the water bath and placed on the bench at room temperature to set up over 24-48 hrs. An elastic hard gel had formed.

Examples 9

Preparation of Chain Extended Water Gellants with 4H-Units

Polyethylene glycol 6000 terminated with aminohexyl groups (20.9 g; entry 6K-6 in Table 1) was dried in vacuo at 80° C. for 2 hours and was subsequently dissolved in chloroform (200 mL) followed by the addition of UPy2 (2.07 g; ca. 1.0 equivalent) in chloroform (40 mL). The reaction mixture was heated to 60° C. and stirred for 4.5 hours under argon. The reaction mixture was cooled down and left under argon overnight. The completion of the reaction was checked by the disappearance of the isocyanate band at 2281 cm-1 in FT-IR. The mixture was diluted with ethanol (500 mL), and evaporation of solvents in vacuo resulted in a white, semi-crystalline, elastic and tough material. NMR-data were in line with the chain extended structure.

The material (0.263 g) was dissolved in THF (4 mL), and water (4.5 mL) was added to get a solids loading of about 5% in water. The clear solution was subsequently put in vacuo to remove the THF, resulting in an elastic hydrogel.

Examples 10

Preparation of 4H-Unit Water Gellants and their Hydrogel Properties

More telechelic and chain extended water gellants based on 4H-units have been prepared than the ones introduced in Examples 8 and 9, and similar synthetic methods as those described there have been used to prepare them. Table 2 shows the two components of these gellants and typifies the hydrogel properties prepared from water and gellant. Method of gel preparation and solids loading of the hydrogel are also given in Table 2, and in the notes below Table 2.

TABLE 2

Prepared water gellants based on the 4H-unit and their hydrogel properties.

| Water Gellant | Prepolymer from example | UPy-building block | Method of gel preparation | Solids Loading$^a$ | Hydrogel properties |
|---|---|---|---|---|---|
| 8A | 6K-10 | UPy1 | A | 7% | soft-elastic |
| 8A | 6K-10 | UPy1 | A | 10% | hard-elastic |
| 8B | 10K-10 | UPy1 | A | 10% | elastic gel |
| 8C | 10K-12 | UPy1 | A | 7% | elastic gel |
| 8C | 10K-12 | UPy1 | A | 10% | hard elastic gel |
| 8D | 20K-10 | UPy1 | A | 14% | elastic gel |
| 8E | 20K-12 | UPy1 | A | 7% | elastic gel |
| 8E | 20K-12 | UPy1 | A | 10% | strong elastic gel |
| 9A | 3K-6 | UPy2 | B | 5% | very elastic |
| 9B | 6K-4 | UPy2 | B | 5% | very elastic |
| 9C | 6K-6 | UPy2 | B | 5% | very elastic (more tough than 9B-gel) |
| 9D | 10K-10c | UPy2 | B | 5% | white, flexible |
| 9E | 10K-12 | UPy2 | B | 5% | very elastic, retaining its shape |
| 9F | 6K-6 + PCL-6 90/10 w/w % | UPy2 | B | 5% | very elastic, rigid, retaining its shape |
| 9G | 6K-6 + PCL-6 80/20 w/w % | UPy2 | B | 5% | very elastic, rigid, retaining its shape |
| 9H | 6K-6 + 3K-6 50/50 w/w % | UPy2 | B | 5% | very elastic |

$^a$solids loading is the weight of water gellant divided by the total weight of the hydrogel.

The telechelic water gellants used for the preparation of gels 8A-8E are all white powders, while the chain extended water gellants used to prepare gels 9A-9H are all white, semi-crystalline, elastic and tough materials.

Details on the preparation of the hydrogels: for telechelic water gellants (UPy1 is used) method A has been applied, while for chain extended water gellants (UPy2 is used) method B has been applied. Method A: the selected gellant from Table 2 was mixed with the desired amount of water and stirred at 55° C. for 12 hours resulting in a homogeneous solution that gelled upon cooling to 25° C. A 24-hour equilibration time was observed. Method B: the gellant material was dissolved in THF (1 g/10 mL) to which the appropriate amount of water was added to get the right solids loading in water. The obtained clear solutions were subsequently put in vacuo to remove the THF, resulting in the hydrogels as described in Table 2.

Hydrogels from particularly gellants 9A-9E and 9H are very elastic as these gels can be elongated for at least three times their lengths (300%-elongation) with recovery to the original shape.

Example 11

Preparation of Telechelic Water Gellants with Urea Units

In similar reaction conditions as those described in Example 8, PEG6000 modified with aminodecyl groups (entry 6K-10 in Table 1) has been end capped with dodecylmonoisocyanate (C12-isocyanate). The material was isolated as a white powder. $^1$H NMR (400 MHz, CDCl$_3$): δ 4.85 (2H), 4.4 (4H), 4.2 (4H), 3.8-3.4 (EO-units), 3.15 (12H), 1.5 (12H), 1.3-1.1 (60H), 0.9 (6H).

Example 12

Preparation of Chain Extended Water Gellants with Urea Units 1,12-Dodecyldiisocyanate (0.12 g; ca. 1.0 equivalent) was added to a solution of PEG6000 modified with aminodecyl groups (3 g; entry 6K-10 in Table 1) in CHCl$_3$ (50 mL). The reaction was allowed to stir overnight at room temperature. FT-IR showed the disappearance of the isocyanate. The CHCl$_3$ solution was concentrated until a noticeable viscosity increase was observed, then precipitation was induced by dilution with diethyl ether under stirring, halting at a ca. 5:1 ether/mother solution ratio. The precipitation mixture was stirred for 20 mins, then allowed to settle prior to filtration and washing with excess ether. The product was dried giving a yield of 95% of a white elastic material. $^1$H NMR (400 MHz, CDCl$_3$): δ 4.85, 4.5, 4.4, 4.2, 3.8-3.4 (EO-units), 3.15, 1.5, 1.3-1.1.

Examples 13

Preparation of Urea-Type Water Gellants and their Hydrogel Properties

More telechelic and chain extended urea-type water gellants have been prepared than the ones introduced in Examples 11 and 12, and similar synthetic methods as those described there have been used to prepare them. Table 3 shows the two components of these gellants, typifies the hydrogel properties prepared from water and the chosen solids loading of the gellant. Method A of gel preparation has been used (see the notes under Table 2).

TABLE 3

Prepared urea-type water gellants and their hydrogel properties

| Water Gellant | Prepolymer from example | Isocyanate building block | Method of gel preparation | Solids Loading$^a$ | Hydrogel properties |
|---|---|---|---|---|---|
| 11A | 6K-10 | C12-NCO | A | 7% | soft |
| 11A | 6K-10 | C12-NCO | A | 12% | elastic |
| 11B | 10K-10 | C12-NCO | A | 7% | tough gel |
| 11B | 10K-10 | C12-NCO | A | 12% | brittle gel |
| 11C | 20K-10 | C12-NCO | A | 11% | elastic gel |
| 11D | 35K-10 | C12-NCO | A | 7% | sticky gel |
| 11D | 35K-10 | C12-NCO | A | 15% | tough gel |
| 12A | 6K-10 | C12-(NCO)2 | A | 7% | elastic gel |

$^a$solids loading is the weight of water gellant divided by the total weight of the hydrogel.

Comparative Example 14

PEG6000 Modified with UPy1

Polyethylene glycol with a molecular weight of 6 kDa (5.78 g) was dried in vacuo at 80° C. for 3 hours and subsequently dissolved in toluene (20 mL) followed by the addition of UPy1 (618 mg) and a few drops of dibutyltin dilaurate. The reaction mixture was heated to 80° C. and stirred for 8 hours under an argon atmosphere, after which 0.5 mL of water was added. After 1 hour, FT-IR analysis showed that the isocyanate band at 2281 cm$^{-1}$ had completely disappeared. The reaction mixture was cooled down, 40 mL of methanol was added, the mixture was filtered over celite and the filtrate concentrated. The product was dissolved in dichloromethane, precipitated in diethylether and dried in vacuum, resulting in a white powder. $^1$H NMR (200 MHz, CDCl$_3$): δ 13.1 (1H), 11.8 (1H), 10.1 (1H), 5.8 (1H), 4.2 (4H), 3.8-3.2 (EO-units), 2.1 (3H), 1.6 (4H), 1.4 (4H).

The white powder (0.134 mg) was dissolved in water (0.54 mL) at 60° C. Upon cooling to room temperature, the 20% solids loadings mixture developed into a hazy viscous solution.

Comparative Example 15

PEG6000 Modified with UPy4

Polyethylene glycol with a molecular weight of 6 kDa (2.02 g) was dried in vacuo at 80° C. for 3 hours and subsequently dissolved in toluene (6 mL) followed by the addition of UPy4 (278 mg) and 1 drop of dibutyltin dilaurate. The reaction mixture was heated to 80° C. and stirred for 8 hours under an argon atmosphere, after which 0.5 mL of water was added. After 1 hour, the isocyanate band at 2281 cm$^{-1}$ had completely disappeared (FT-IR analysis). The reaction mixture was cooled down, 20 mL of methanol was added, the suspension was filtered over celite and the filtrate was concentrated. The product was dissolved in dichloromethane and precipitated in diethylether, resulting in a white powder. $^1$H NMR (200 MHz, CDCl$_3$): δ δ 13.1 (2H), 11.8 (2H), 10.1 (2H), 5.8 (2H), 4.2 (8H), 3.8-3.2 (EO-units), 2.1 (6H), 1.6 (8H), 1.4 (16H).

The white powder was dissolved at 60° C. in the appropriate amount of water to get the right solids loading, and was thereafter cooled to room temperature. A 10% loading gave a hazy low viscous solution, a 20% loading gave a hazy paste and a 30% loading gave a weak and brittle hazy paste.

Comparative Example 16

PEG6000 Chain Extended with UPy2

Telechelic hydroxy terminated PEG-6000 (10.20 g) was heated in vacuo in a 3-neck flask to 120° C. for 120 minutes and subsequently cooled down to 80° C. UPy2 (1.25 g; 1.2 equivalents) and two drops of dibutyl tin dilaurate dissolved in toluene (40 mL) were added to the polymer melt and the solution was stirred overnight under argon at 80° C. The reaction mixture was diluted with 40 mL THF and precipitated into diethylether. The material is white (semi-crystalline), elastic and tough. $^1$H NMR (300 MHz, CDCl$_3$/CD$_3$OD): δ 4.1, 3.6, 2.8, 2.2, 1.8-1.4, 1.2-0.8.

The prepared PEG-UPy2 block copolymer was dissolved in THF (1 g/10 mL) to which the appropriate amount of water was added to get the right solids loading. These clear solutions were subsequently put in vacuo to remove the THF, resulting in the different hydrogels as described in Table 4 below.

Comparative Example 17

Amino Ethyl Terminated PEG3800 Chain Extended with UPy2

Amino ethyl terminated PEG with a molecular weight of 3.8 kDa (1.75 g) was heated at 80° C. in vacuo over P$_2$O$_5$ for 1 hour, was subsequently cooled down to 60° C., and was then dissolved in chloroform (20 mL). UPy2 (285 mg; ca. 1.0 equivalent) in chloroform (20 mL) was slowly added to the solution. After 1 hour the isocyanate band at 2281 cm⁻¹ had completely disappeared (FT-IR-analysis). Ninhydrin staining showed the presence of amine, and therefore another 19 mg of UPy2 was added. After stirring for 1 hour at 60° C. the product was recovered by evaporation of the solvent.

The material (736 mg) was dissolved in THF (1 g/10 mL) to which 14 mL of water was added to get a solids loading of 5%. This clear solution was subsequently put in vacuo to remove the THF, resulting in a viscous solution. See also Table 4 below.

Example 18

Conclusions for Comparative Examples 14, 15, 16 and 17

Above comparative examples 14 and 15 show that telechelic PEG-materials to which two 4H-units are directly attached (i.e. no linker L is incorporated into the water gellant structure) are not efficient in making strong and/or elastic hydrogels. In fact, below 20% solid loadings of these materials in water, no hydrogel formation is observed. Compare these findings with the results compiled in Table 2 for hydrogels of this invention prepared from gellants 8A-8E.

In the comparative examples 16 and 17 (see Table 4), telechelic PEG-materials are chain extended with 4H-units without the use of linkers L. Hydrogels can be prepared from these materials, but as data in Table 2 for hydrogels from gellants 9A-9H indicate, at similar solid loadings, the gels of this invention give better mechanical properties (e.g. toughness, elasticity). Or, similar strengths can be attained with lower solids loadings.

Additionally, the gels of this invention have been prepared without the use of a toxic Sn-catalyst, in contrast to the materials from comparative examples 14, 15 and 16.

TABLE 4

Hydrogel formulations for comparative examples 16 and 17

| Hydrogel Example | Prepolymer | UPy-building block | Method of gel preparation | Solids Loading | Hydrogel properties |
|---|---|---|---|---|---|
| 16A | PEG6000[a] | UPy2 | B | 5% | soft, flexible |
| 16B | PEG6000[a] | UPy2 | B | 10% | flexible, elastic |
| 16C | PEG6000[a] | UPy2 | B | 20% | hard, flexible |
| 17 | PEG3800[b] | UPy2 | B | 5% | viscous solution |

[a]hydroxy functional and telechelic;
[b]amine functional and telechelic

Comparative Example 19

Chain Extended PEG6000

Telechelic hydroxy terminated PEG-6000 (5.14 g) together with 2-amino-4-hydroxy-5-(β-hydroxy ethyl)-6-methylpyrimidine (0.174 g) and one drop of dibutyl tin dilaurate was heated in vacuo in a Schlenk flask at 100° C. for 120 minutes and subsequently cooled to 50° C. and dissolved in 5 mL xylene. Subsequently, IPDI (0.381 g) was added to this solution followed by stirring overnight under argon for 50° C. The reaction mixture was diluted with propylenecarbonate (2 mL) and heated to 140° C. while stirring under argon for 2 hours. The reaction mixture was cooled, diluted with THF, filtered, and precipitated in diethyl ether. After drying in vacuo, a white elastic and tough material was obtained.

The prepared PEG-UPy block copolymer was dissolved in THF (1 g/10 mL) to which the appropriate amount of water was added to get 10 weight % solids loading in water. This clear solution was subsequently put in vacuo to remove the THF, resulting in a hydrogel comparable to Comparative Example 16B.

Comparative Example 20

Telechelic PEG20000

Telechelic hydroxy terminated PEG-20000 (7.28 g) together with 2-amino-4-hydroxy-6-methylpyrimidine (0.122 g) and one drop of dibutyl tin dilaurate was heated in vacuo in a Schlenk flask at 100° C. for 120 minutes and subsequently cooled to 70° C. and dissolved in xylene (10 mL). Subsequently, 4,4'-methylenebis(cyclohexyl isocyanate) (0.191 g) was added to this solution followed by stirring overnight under argon for 70° C. The reaction mixture was diluted with propylenecarbonate (2 mL) and heated to 140° C. while stirring under argon for 2 hours. The reaction mixture was cooled down, diluted with THF, filtered, and precipitated into diethyl ether. After drying in vacuo, a white solid was obtained.

The prepared telechelic UPy-PEG-UPy was dissolved in THF (1 g/10 mL) to which the appropriate amount of water was added to get a 2 weight % solids loading in water. This clear solution was subsequently put in vacuo to remove the THF, resulting in a low viscous aqueous solution.

The invention claimed is:

1. A hydrogel comprising:

(a) 0.3-50.0 wt. %, based on the total weight of the hydrogel, of a water gellant comprising a polymer backbone P having the structure according to formula (A) or formula (B):

P[L-(4H)]$_n$     (A)

or

[P-L-(4H)-L-]$_p$     (B)

wherein:

n is in the range of 1.8 to 10;

p is in the range of 2 to 25;

L is a hydrophobic linker selected from the group consisting of cyclic, linear or branched $C_2$-$C_{24}$ alkylene groups, $C_6$-$C_{24}$ arylene groups, $C_7$-$C_{24}$ alkarylene groups and $C_7$-$C_{24}$ arylalkylene groups, wherein the alkylene groups, arylene groups, alkarylene groups and arylalkylene groups optionally, comprise 1-5 heteroatoms selected from the group consisting of O, N and S, wherein said hydrophobic linker L is covalently connected to the 4H-unit via a urea, thiourea, urethane, thiourethane, amide, ester, carbonate, secondary amine, tertiary amine or ether moiety, and wherein the polymer backbone P and the hydrophobic linker L are connected via a urea, thiourea, urethane, thiourethane, amide, carbonate, secondary amine or tertiary amine moiety; and wherein 4H represents the 4H-unit that has the general formula (1) or (2):

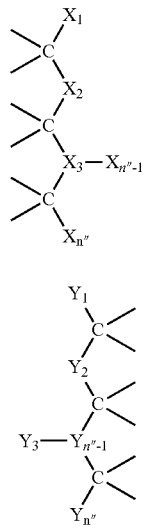

wherein the C—$X_i$ and the C—$Y_i$ linkages each represent a single or double bond, n" is 4 or more, and $X_i$ represent donors or acceptors that form hydrogen bridges with the H-bridge forming monomeric unit containing a corresponding general form (2) linked to them with $X_i$ representing a donor and $Y_i$ an acceptor and vice versa; and (b) 50.0 to 99.7 wt. % water.

2. The hydrogel according to claim 1, wherein the 4H-unit has the general formula (3) or formula (4) and tautomers thereof:

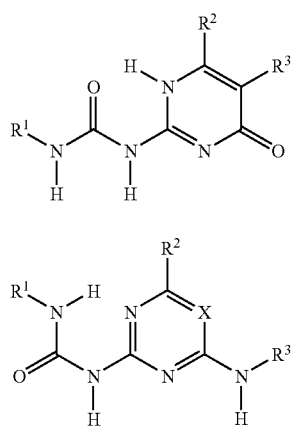

wherein X is nitrogen atom or a carbon atom bearing a substituent $R^{15}$ and wherein $R^1$, $R^2$, $R^{15}$ and $R^3$ are independently selected from the group consisting of:

(i) hydrogen;
(ii) $C_1$-$C_{20}$ alkyl;
(iii) $C_6$-$C_{12}$ aryl;
(iv) $C_7$-$C_{12}$ alkaryl;
(v) $C_7$-$C_{12}$ alkylaryl;
(vi) polyester groups having the formula (5)

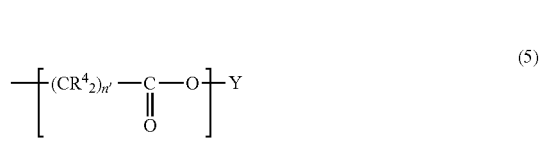

wherein $R^4$ and Y are independently selected from the group consisting of hydrogen and $C_1$-$C_6$ linear or branched alkyl, n' is 1-6 and m is 10 to 100;

(vii) $C_1$-$C_{10}$ alkyl groups substituted with 1-4 ureido groups according to the formula (6)

wherein $R^5$ is selected from the group consisting of hydrogen and $C_1$-$C_6$ linear or branched alkyl;

(viii) polyether groups having the formula (7)

wherein Y, $R^6$ and $R^7$ are independently selected from the group consisting of hydrogen and $C_1$-$C_6$ linear or branched alkyl and o is 10-100; and wherein the 4H-unit is bonded to a polymer backbone via $R_1$, $R_2$ and/or $R_3$ (so that $R_1$, $R_2$ or $R_3$ represent a direct bond) with the other R groups representing, independently a side chain according to (i)-(viii).

3. The hydrogel according to claim 1, wherein the water gellant has a molecular weight of 1,200 to 1,000,000.

4. The hydrogel according to claim 2, wherein the water gellant has a molecular weight of 1,200 to 1,000,000.

5. The hydrogel according to claim 1, wherein the polymer backbone P and the hydrophobic linker L are connected via a urea or urethane moiety.

6. The hydrogel according to claim 1, wherein the hydrophobic linker L is connected to the 4H-unit via a urea or amide moiety.

7. The hydrogel according to claim 1, wherein the water gellant has the formula (A) or the formula (B):

or

obtained by:
(a) converting a polymer backbone P into a prepolymer according to the formula P-[L]$_n$,
(b) introducing the 4H-unit at the termini of the hydrophobic linker moiety L, wherein P, L and the 4H-unit are connected to each other by moieties selected from the group consisting of urea, thiourea, urethane, thiourethane, amide, ester, carbonate, secondary amine, tertiary amine and ether moieties.

8. The hydrogel according to claim 1, wherein the water gellant has the formula (A) or the formula (B), $$P\text{-}[L\text{-}(4H)]_n \quad (A)$$

or $$[P\text{-}L\text{-}(4H)\text{-}L\text{-}]_p \quad (B)$$

obtained by:
(a) functionalizing a hydrophobic linker L at a first terminus thereof with a 4H-unit to provide a building block having the structure $4H\text{-}[L]_q$, wherein q represents the number of hydrophobic linker groups L attached to the 4H-unit and wherein q is 1 or 2, wherein the hydrophobic linker has a functional group at another terminus, and
(b) connecting the building block to the polymer backbone P.

9. The hydrogel according to claim 1, wherein the polymer backbone P as comprised by the water gellant has a molecular weight of 250 to 200,000.

10. The hydrogel according to claim 7, wherein the polymer backbone P has the formula $P\text{—}(OH)_n$, wherein n is in the range of 1.8 to 10.

11. The hydrogel according to claim 10, wherein the polymer backbone P has the formula $P\text{—}(OH)_2$.

12. The hydrogel according to claim 10, wherein polymer backbone P is telechelic.

13. The hydrogel according to claim 11, wherein polymer backbone $P\text{—}(OH)_2$ is selected from the group consisting of polyethers, polyesters, polyamides, polycarbonates, polysiloxanes, hydrogenated polyolefins, polyortho esters, lower molecular weight materials that are derived from dimerized fatty acids, or copolymers of these polymers.

14. The hydrogel according to claim 11, wherein polymer backbone $P\text{—}(OH)_2$ is a polyethylene glycol.

15. The hydrogel according to claim 10, wherein polymer backbone $P\text{—}(OH)_n$ is prepared from polymers obtainable by (co)polymerization of vinyl monomers, the vinyl monomers being selected from the group consisting of:
(a) monomers according to the formula (8)

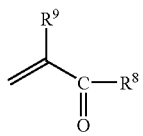

(8)

wherein $R^8$ is independently selected from the group consisting of:
(i) OH;
(ii) $C_1$-$C_{12}$ linear or branched alkoxy, optionally substituted with 1-6 hydroxy groups;
(iii) amide according to the formula $\text{—}N(R^{10})_2$ wherein $R^{10}$ can be hydrogen or $C_1$-$C_6$ linear or branched alkyl, optionally substituted with 1-6 hydroxy groups;
(iv) ammonium salt according to the formula) $\text{—}[N(R^{10})_3]^+X^-$, wherein $R^{10}$ is as defined for (iii) and X is a halogen atom; and
(v) a group according to the formula (9)

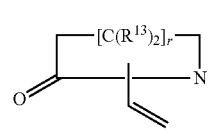

(9)

wherein $R^{10}$ is as defined for (iii) and p is 1-50 and q=2 or 3; and
wherein $R^9$ is hydrogen or methyl;
(b) $C_1$-$C_{12}$ linear or branched alkyl vinyl ether;
(c) vinyl alcohol;
(d) $C_2$-$C_{12}$ α-alkenylene ω-sulfonate having an alkaline earth metal cation or an alkali metal cation;
(e) $C_7$-$C_{12}$ vinylaryl sulfonate according to formula (10)

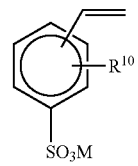

(10)

wherein $R^{10}$ is as defined for (iii) and M is an alkaline earth metal or an alkali metal cation;
(f) $CH_2\!=\!CH\text{—}R^{11}$, wherein $R^{11}$ is selected from the group consisting of: pyrrolyl, imidazolyl, pyrazolyl, pyridinyl, pyrazinyl, pyrimidinyl, pyrrolidyl, indolyl, indolizinyl, indazolyl, purinyl, quinolizinyl, quinolinyl, isoquinolinyl, phthalizinyl, naphtypyridinyl, quinoxalinyl, quinazolinyl, cinnolinyl, pteridinyl, pyrrolidonyl, pyrrolinyl, pyrrolidinyl, imidazolidinyl, imidazolinyl, pyrazolidinyl, pyrazolinyl, piperidyl, piperazinyl, indolinyl, isoindolinyl, morpholinyl, isoxazolyl, furazinyl, and isothiazolyl;
(g) $CH_2\!=\!CH\text{—}O\text{—}C(O)R^{12}$, wherein $R^{12}$ is selected from the group consisting of $C_1$-$C_6$ linear or branched alkyl;
(h) $CH_2\!=\!CH\text{—}CH_2OR^{13}$, wherein $R^{13}$ is selected from the group consisting of hydrogen and $C_1$-$C_6$ linear or branched alkyl; and
(i) N-vinyl lactams according to the formula (11)

(11)

wherein $R^{13}$ is as defined for (h) and r is 2-6.

16. The hydrogel according to claim 1, which further comprises a biologically active or pharmaceutically active compound or a bioactive species.

17. A pharmaceutical or a biomedical composition comprising the hydrogel according to claim 1.

18. The hydrogel according to claim 6, wherein the hydrophobic linker L is selected from the group consisting of cyclic, linear or branched $C_4$-$C_{20}$ alkylene groups and $C_6$-$C_{20}$ arylene groups.

19. The hydrogel according to claim 6, wherein the hydrophobic linker L is a $C_6$-$C_{12}$ alkylene group.

20. The hydrogel according to claim 7, wherein the hydrophobic linker L in the prepolymer $P\text{-}[L]_n$ is terminated with an amine moiety.

21. The hydrogel according to claim 8, wherein the hydrophobic linker L in the building block $4H\text{-}[L]_q$ is terminated with an amine moiety.

22. The hydrogel according to claim 1, wherein the hydrophobic linker L is flanked by two amine moieties.

* * * * *

UNITED STATES PATENT AND TRADEMARK OFFICE
CERTIFICATE OF CORRECTION

PATENT NO. : 8,628,789 B2 Page 1 of 1
APPLICATION NO. : 12/053404
DATED : January 14, 2014
INVENTOR(S) : Baughman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1244 days.

Signed and Sealed this
Thirtieth Day of May, 2017

Michelle K. Lee
*Director of the United States Patent and Trademark Office*